United States Patent
Borrelli et al.

(10) Patent No.: US 6,884,626 B1
(45) Date of Patent: *Apr. 26, 2005

(54) REDRAWN CAPILLARY IMAGING RESERVOIR

(75) Inventors: Nicholas F. Borrelli, Elmira, NY (US); Alain R. E. Carre, Le Chatelet-en-Brie (FR); Thierry L. A. Dannoux, Avon (FR); Bernard Eid, Corning, NY (US); David Root, Lexington, MA (US); Raja Rao Wusirika, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/525,920

(22) Filed: Mar. 15, 2000

Related U.S. Application Data

(63) Continuation-in-part of application No. 09/300,121, filed on Apr. 27, 1999, now Pat. No. 6,350,618, and a continuation-in-part of application No. 09/299,766, filed on Apr. 26, 1999, now Pat. No. 6,596,237.
(60) Provisional application No. 60/091,707, filed on Jul. 3, 1998.

(30) Foreign Application Priority Data

Apr. 27, 1998 (EP) .............................................. 98401021

(51) Int. Cl.[7] .............................. G01N 1/16; G01N 1/26; G01N 1/00; G01N 1/10; B01L 3/02
(52) U.S. Cl. ....................... 436/180; 436/174; 422/100; 422/99; 422/102; 73/863.31; 73/864
(58) Field of Search .......................... 422/99, 100, 102; 73/863.31, 863.81, 864.01, 864.31; 400/124.1; 101/93.37, 97, 98, 333; 436/180

(56) References Cited

U.S. PATENT DOCUMENTS 3,568,735 A 3/1971 Lancaster .................... 141/238
3,863,507 A 2/1975 Jones et al. ................ 73/423 A (Continued)

FOREIGN PATENT DOCUMENTS

DE 196 28 928 1/1998
DE 197 40 263 A1 5/1998

(Continued)

OTHER PUBLICATIONS

A.M. Bray, N.J. Maeji, R.M. Valerio, R.A. Campbell, H. M. Geysen, Direct Cleavage of Peptides from a Solid Support into Aqueous Buffer—Application in Simultaneous Multiple Peptide Synthesis, *J. Org. Chem.*, 1991, 56, pp 6659–6666.

(Continued)

*Primary Examiner*—Jill Warden
*Assistant Examiner*—Brian R Gordon
(74) *Attorney, Agent, or Firm*—Foley & Lardner

(57) ABSTRACT

Methods and apparatus for depositing a high density biological or chemical array onto a solid support. Specifically, the apparatus is made up of a plurality of open ended channels collectively forming a matrix. The matrix has been redrawn and cut such that the pitch of the channels on the loading end is larger than the pitch of the channels on the liquid delivery end. The upper portion of each channel serves as a reservoir, while the opposing end, which has been formed by the redrawing process, is diametrically sized such that liquid in the reservoir is retained by capillary pressure at the delivery end. At any point along the height of the capillary reservoir device, all cross-sectional dimensions and areas are uniformly reduced. In other words, the on-center orientation of any two channels, also referred to as the pitch between 2 channels, measured as a function of the diameter of any cross section, is constant throughout the structure. The liquid within the channels is either printed directly from the tool onto a substrate or transferred to a substrate by a typographical pin plate. In another embodiment, the device may be used in transferring sample between multiwell plates of different well density.

67 Claims, 12 Drawing Sheets

U.S. PATENT DOCUMENTS

| | | | | |
|---|---|---|---|---|
| 4,010,019 | A | 3/1977 | Cole et al. | |
| 4,106,911 | A | 8/1978 | Marcelli | 23/259 |
| 4,140,018 | A | 2/1979 | Maldarelli et al. | 73/423 A |
| 4,199,013 | A | 4/1980 | Reich et al. | 141/130 |
| 4,216,245 | A | 8/1980 | Johnson | |
| 4,224,278 | A | 9/1980 | Hogen Esch | |
| 4,276,048 | A | 6/1981 | Leaback | 23/230 R |
| 4,334,879 | A | 6/1982 | Fujimori | 23/230 R |
| 4,416,400 | A | 11/1983 | Dougherty, Sr. | |
| 4,422,151 | A | 12/1983 | Gilson | 364/496 |
| 4,446,104 | A | 5/1984 | Hämmerling et al. | |
| 4,459,265 | A | 7/1984 | Berglund | 422/64 |
| 4,461,328 | A | 7/1984 | Kenney | |
| 4,483,925 | A | 11/1984 | Noack | 435/293 |
| 4,621,655 | A | 11/1986 | Roche | |
| 4,621,665 | A | 11/1986 | Webb | 141/1 |
| 4,699,884 | A | 10/1987 | Noss et al. | 435/287 |
| 4,731,335 | A | 3/1988 | Brigati | 436/180 |
| 4,853,020 | A | 8/1989 | Sink | |
| 4,906,439 | A | 3/1990 | Grenner | |
| 4,914,022 | A | 4/1990 | Furmanski et al. | |
| 4,950,391 | A | 8/1990 | Weickhardt | |
| 5,000,921 | A | 3/1991 | Hanaway et al. | 422/100 |
| 5,008,082 | A | 4/1991 | Shaw | 422/65 |
| 5,038,039 | A | 8/1991 | Wong et al. | |
| 5,041,266 | A | 8/1991 | Fox | |
| 5,055,263 | A | 10/1991 | Meltzer | 422/65 |
| 5,095,213 | A | 3/1992 | Strongin | |
| 5,166,889 | A | 11/1992 | Cloyd | 364/510 |
| 5,188,148 | A | 2/1993 | Garrison | 137/606 |
| 5,188,733 | A | 2/1993 | Wang et al. | |
| 5,262,128 | A | 11/1993 | Leighton et al. | 422/100 |
| 5,265,327 | A | 11/1993 | Faris et al. | |
| 5,334,352 | A | 8/1994 | Johnson | 422/99 |
| 5,338,688 | A | 8/1994 | Deeg et al. | 436/180 |
| 5,445,934 | A | 8/1995 | Fodor et al. | |
| 5,474,796 | A | 12/1995 | Brennan | 427/2.13 |
| 5,498,545 | A | 3/1996 | Vestal | |
| 5,508,200 | A | 4/1996 | Tiffany et al. | |
| 5,510,270 | A | 4/1996 | Fodor et al. | 436/518 |
| 5,547,839 | A | 8/1996 | Dower et al. | |
| 5,551,487 | A | 9/1996 | Gordon et al. | 141/1 |
| 5,560,811 | A | 10/1996 | Briggs et al. | |
| 5,577,444 | A | 11/1996 | Toyama | |
| 5,583,211 | A | 12/1996 | Coassin et al. | |
| 5,585,275 | A | 12/1996 | Hudson et al. | |
| 5,602,197 | A | 2/1997 | Johnson et al. | 524/275 |
| 5,624,775 | A | 4/1997 | Carre et al. | |
| 5,632,957 | A | 5/1997 | Heller et al. | |
| 5,637,126 | A | 6/1997 | Ema et al. | |
| 5,649,576 | A | 7/1997 | Kirk et al. | |
| 5,678,165 | A | 10/1997 | Wu | |
| 5,700,637 | A | 12/1997 | Southern | |
| 5,719,023 | A | 2/1998 | Zarling et al. | |
| 5,723,320 | A | 3/1998 | Dehlinger | |
| 5,736,105 | A | 4/1998 | Astle | 422/100 |
| 5,744,305 | A | 4/1998 | Fodor et al. | |
| 5,756,050 | A | 5/1998 | Ershow et al. | 422/100 |
| 5,763,170 | A | 6/1998 | Raybuck | |
| 5,770,151 | A | 6/1998 | Roach et al. | 422/63 |
| 5,770,860 | A | 6/1998 | Franzen | |
| 5,772,966 | A | 6/1998 | Maracas et al. | 422/100 |
| 5,774,779 | A | 6/1998 | Tuchinskiy | |
| 5,807,522 | A | 9/1998 | Brown et al. | |
| 5,843,767 | A | 12/1998 | Beattie | |
| 5,882,930 | A | 3/1999 | Baier | 436/49 |
| 5,916,526 | A * | 6/1999 | Robbins | 422/102 |
| 5,972,545 | A | 10/1999 | Eid et al. | |
| 5,974,969 | A | 11/1999 | Okumura et al. | |
| 6,030,829 | A | 2/2000 | Dannoux et al. | |
| 6,051,190 | A * | 4/2000 | Birch et al. | |
| 6,054,325 | A | 4/2000 | Keder et al. | |
| 6,083,763 | A | 7/2000 | Balch | |
| 6,090,251 | A | 7/2000 | Sundberg et al. | |
| 6,189,450 | B1 | 2/2001 | Shih | |
| 6,221,653 | B1 | 4/2001 | Caren et al. | |
| 6,228,659 | B1 | 5/2001 | Kowallis et al. | |
| 6,231,739 | B1 | 5/2001 | Nordman et al. | |
| 6,231,813 | B1 * | 5/2001 | Ally et al. | |
| 6,238,626 | B1 | 5/2001 | Higuchi et al. | |
| 6,254,826 | B1 | 7/2001 | Acosta et al. | |
| 6,255,116 | B1 | 7/2001 | Leber et al. | |
| 6,255,119 | B1 | 7/2001 | Baier | |
| 6,299,958 | B1 | 10/2001 | St. Julien et al. | |
| 6,331,441 | B1 | 12/2001 | Balch et al. | |
| 6,350,618 | B1 | 2/2002 | Borrelli et al. | |
| 2001/0044157 | A1 * | 11/2001 | Shaion et al. | |
| 2001/0049149 | A1 * | 12/2001 | Kennedy et al. | |

FOREIGN PATENT DOCUMENTS

| | | |
|---|---|---|
| FR | 2 741 357 | 5/1997 |
| FR | 2 754 469 | 4/1998 |
| FR | 2760838 | 9/1998 |
| FR | 2764705 | 12/1998 |
| JP | 59-120437 | 7/1984 |
| JP | 63-199432 | 8/1988 |
| JP | 63199432 | 8/1988 |
| JP | 6-294771 | 10/1994 |
| WO | WO 93/09872 | 5/1993 |
| WO | WO 95/25116 A1 | 9/1995 |
| WO | 95/34575 | 12/1995 |
| WO | 95/35505 | 12/1995 |
| WO | 97/15394 | 5/1997 |
| WO | 97/19749 | 6/1997 |
| WO | 97/40383 | 10/1997 |
| WO | 97/45730 | 12/1997 |
| WO | 97/49987 | 12/1997 |
| WO | 98/14770 | 4/1998 |
| WO | WO 98/15355 | 4/1998 |
| WO | 98/16830 | 4/1998 |
| WO | 98/29736 | 7/1998 |
| WO | 98/40466 | 9/1998 |
| WO | WO 98/57747 | 12/1998 |

OTHER PUBLICATIONS

S.R. Wilson, A. W. Czarnik, *Combinatorial Chemistry Synthesis and Application*, John Wiley & Sons, Inc., 1997 (Table of Contents).

*Handbook of Manual Microtiter Procedures* Ch. 1, pp. 1–27 (T B Conrath & N B Coupe eds., 2d ed. 1978).

J. Stanchfield et al., "Precision 96–Channel Dispenser for Microchemical Techniques," *BioTechniques*, vol. 20, No. 2, pp. 292–296 (Feb. 1996).

"Automation Increases Progress In Genetic Research," 3 pp., available at http://www.llnl.gov/automation–robotics/automation.html (last modified Oct. 9, 1997).

V. Holland, Beckman Biomek Interface archives, 1 pp., available at http//discuss.foresight.org/critmail/sci_nano/3819.html (Jun. 19, 1997).

M. Schummer et al., "Inexpensive Handheld Device for the Construction of High–Density Nucleic Acid Arrays," *BioTechniques*, col. 23, No. 6, pp. 1087–1090, 1092 (Dec. 1997).

* cited by examiner

48

50

US 6,884,626 B1

REDRAWN CAPILLARY IMAGING RESERVOIR

This application is a continuation-in-part of U.S. application Ser. No. 09/299,766 filed on Apr. 26, 1999, now U.S. Pat. No. 6,596,237, which claims the benefit both of Provisional Application No. 60/091,707 filed on Jul. 3, 1998 and of European Application No. 98401021.5 filed on Apr. 27, 1998, and this application also is a continuation-in-part of U.S. application Ser. No. 09/300,121 filed on Apr. 29, 1999, now U.S. Pat. No. 6,350,618, which claims the benefit of both Provisional Application No. 60/091,707 filed on Jul. 3, 1998 and of European Application number 98401021.5 filed on Apr. 27, 1998.

FIELD OF INVENTION

The invention relates to a device and method for the printing of high density arrays for use in biological and chemical assays as well as a device that can be used in sample transfer between multiwell plates of differing well density.

BACKGROUND OF INVENTION

Hybridization is a hydrogen- bonding interaction between two nucleic acid strands that obey the Watson-Crick complementary rules. All other base pairs are mismatches that destabilize hybrids. Since a single mismatch decreases the melting temperature of a hybrid by up to 10° C., conditions can be found in which only perfect hybrids can survive. Hybridization comprises contacting the strands, one of which is usually immobilized on a solid support and the other usually bears a radioactive, chemiluminescent or fluorescent label, and then separating the resulting hybrids from the unreacted labeled strands by washing the support. Hybrids are recognized by detecting the label bound to the surface of the support.

Oligonucleotide hybridization is widely used to determine the presence in a nucleic acid of a sequence that is complimentary to the oligonucleotide probe. In many cases, this provides a simple, fast, and inexpensive alternative to conventional sequencing methods. Hybridization does not require nucleic acid cloning and purification, carrying out base-specific reactions, or tedious electrophoretic separations. Hybridization of oligonucleotide probes has been successfully used for various purposes, such as analysis of genetic polymorphisms, diagnosis of genetic diseases, cancer diagnostics, detection of viral and microbial pathogens, screening of clones, genome mapping and ordering of fragment libraries.

An oligonucleotide array is comprised of a number of individual oligonucleotide species tethered to the surface of a solid support in a regular pattern, each species in a different area, so that the location of each oligonucleotide is known. An array can contain a chosen collection of oligonucleotides, e.g., probes specific for all known clinically important pathogens or specific for all known clinically important pathogens or specific for all known sequence markers of genetic diseases. Such an array can satisfy the needs of a diagnostic laboratory. Alternatively, an array can contain all possible oligonucleotides of a given length n. Hybridization of a nucleic acid with such a comprehensive array results in a list of all its constituent n-mers, which can be used for unambiguous gene identification (e.g., in forensic studies), for determination of unknown gene variants and mutations (including the sequencing of related genomes once the sequence of one of them is known), for overlapping clones, and for checking sequences determined by conventional methods. Finally, surveying the n-mers by hybridization to a comprehensive array can provide sufficient information to determine the sequence of a totally unknown nucleic acid.

Oligonucleotide arrays can be prepared by synthesizing all the oligonucleotides, in parallel, directly on the support, employing the methods of solid-phase chemical synthesis in combination with site-directing masks as described in U.S. Pat. No. 5,510,270. Four masks with non-overlapping windows and four coupling reactions are required to increase the length of tethered oligonucleotides by one. In each subsequent round of synthesis, a different set of four masks is used, and this determines the unique sequence of the oligonucleotides synthesized in each particular area. Using an efficient photolithographic technique, miniature arrays containing as many as $10^5$ individual oligonucleotides per $cm^2$ of area have been demonstrated.

Another technique for creating oligonucleotide arrays involves precise drop deposition using a piezoelectric pump as described in U.S. Pat. No. 5,474,796. The piezoelectric pump delivers minute volumes of liquid to a substrate surface. The pump design is very similar to the pumps used in ink jet printing. This picopump is capable of delivering 50 micron diameter (65 picoliter) droplets at up to 3000 Hz and can accurately hit a 250 micron target. The pump unit is assembled with five nozzles array heads, one for each of the four nucleotides and a fifth for delivering activating agent for coupling. The pump unit remains stationary while droplets are fired downward at a moving array plate. When energized, a microdroplet is ejected from the pump and deposited on the array plate at a functionalized binding site. Different oligonucleotides are synthesized at each individual binding site based on the microdrop deposition sequence.

Another approach using arrays is the pin dipping method for parallel oligonucleotide synthesis. Geysen, *J. Org. Chem.* 56, 6659 (1991). In this method, small amounts of solid support are fused to arrays of solenoid controlled polypropylene pins, which are sequentially dipped into trays of the appropriate reagents. The density of the arrays is limited by this process.

Further approaches to forming an array involve taking presynthesized oligonucleotide or cDNA sequences from separately prepared aqueous mixtures and transferring them to substrate either individually or in some small multiple. This may be accomplished for example by repeatedly contacting a substrate surface with typographic pins holding droplets, using ink jet printing mechanisms to lay down an array matrix, or by use of a pen plotter. These printing processes are limited by the time and expense required in transferring $10^3$ or greater different sequence mixtures onto defined positions on a substrate.

SUMMARY OF INVENTION

The present invention provides a capillary reservoir device and liquid deposition tool and methods for depositing a high density biological or chemical array onto a substrate. The tool is made up of a plurality of open ended channels collectively forming a matrix. The matrix has been redrawn and cut such that the pitch of the channels on the loading end is far larger than the pitch of the channels on the liquid delivery end. The upper portion of each channel serves as a reservoir, while the opposing end, which has been formed by the redrawing process, is diametrically sized such that liquid in the reservoir is retained by capillary pressure at the delivery end. At any point along the height of the capillary reservoir device, all cross-sectional dimensions and areas are uniformly reduced. In other words, the on-center orientation of any two channels, also referred to as the pitch between 2 channels, measured as a function of the diameter of any cross section, is constant throughout the structure. In another embodiment, a variation of the device of the present invention may be used in transferring sample between multiwell plates of different well density.

DETAILED DESCRIPTION OF THE INVENTION

Printing Tool

Figure 1:
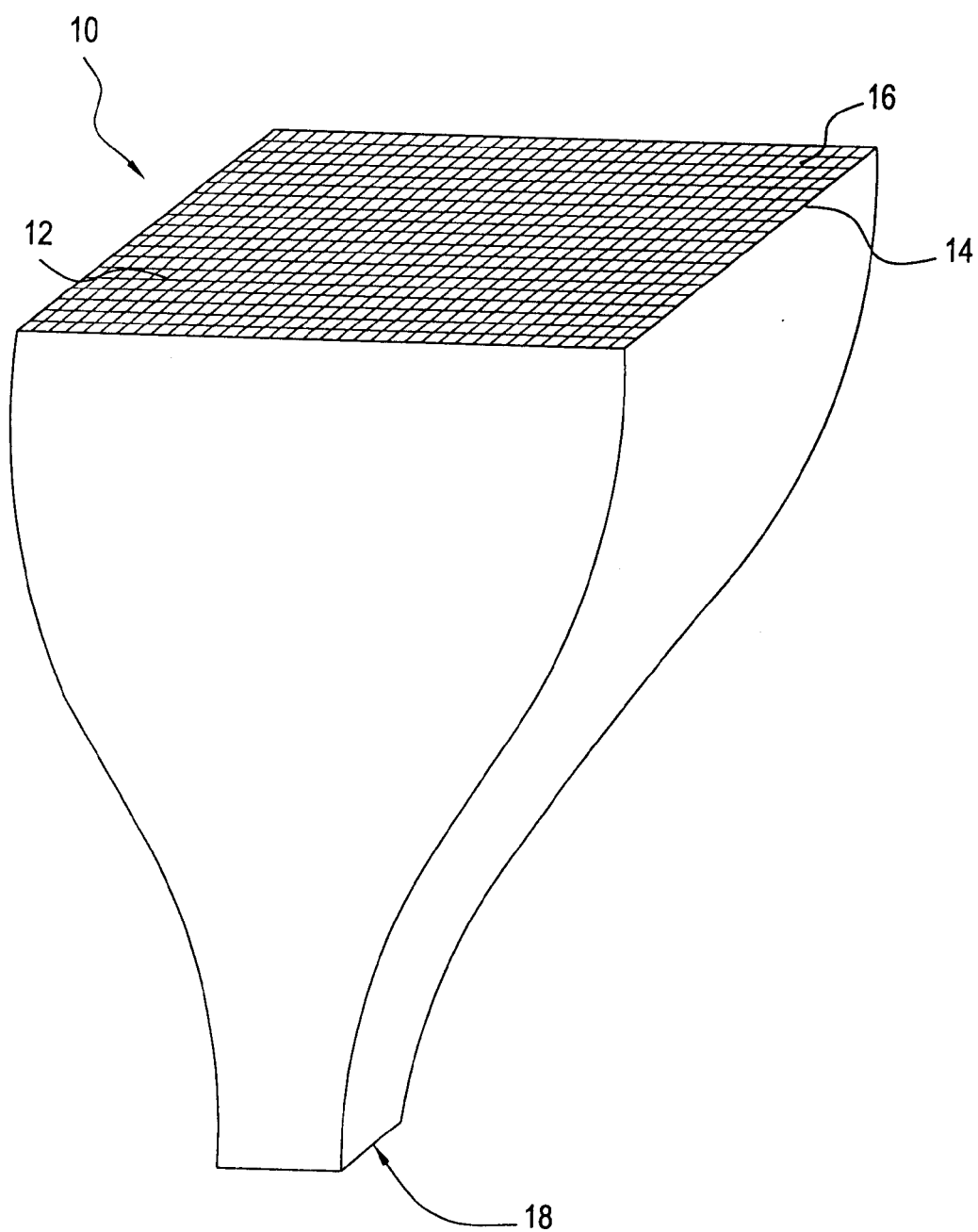
FIG. 1 is a three dimensional view of the device of the present invention.

Glass and organic polymer redraw processes are well known and have been used to form precision tubing, sheets and fiber bundles with complex cross sections. The present invention adapts the known redraw technique in a unique way to form a container having an array of channels that can individually deliver small volumes of liquid either onto a substrate, to a typographic pinplate, or into wells of a multiwell plate.

The redraw technique is instituted on a multi-celled extruded block, also referred to as a honeycomb substrate, or a collection of connected capillary tubes. An important aspect of the redraw technique is that relatively large glass or polymer structures having complex cross-sectional configurations, corresponding to complex cross-sectional configurations of the final product may be easily formed to desired dimensions. During the redrawing or stretching process, all cross-sectional dimensions and areas are uniformly reduced while the present tolerance remains constant. Thus, for purposes of illustration, a 1 inch dimension having a tolerance of 1% e.g., ±0.01 inch, in a 10 to 1 reduction results in a 0.1 inch dimension and a tolerance of ±0.001 inch. A further 10 to 1 reduction results in a 0.01 inch dimension and a tolerance of ±0.0001 inch.

In order to form a capillary reservoir device from glass, glass ceramic, or ceramic material, one must use a thermoplastic binder such as paraffin wax or a binder as described in U.S. Pat. No. 5,602,197, incorporated herein by reference, and combine it with an inorganic powdered material, preferably PYREX 7761 powder with frit size centered on 10 $\mu$m. This organic/inorganic mixture is then extruded through a counter rotating twin screw extruder, operated at room temperature. A die determines the dimensions of the extruded material. Preferably, a 2–7 inch diameter, square or round channeled, monolithic honeycomb preform with 25–15 mil channel walls and 200–400 cells per square inch of frontal area results from the extrusion. The preform may be extruded in either round, rectangular or square cross sectional shape. The cross sectional shape of the cells may be any shape as determined by the die. The organic binder must be carefully removed by heating slowly to a sufficient temperature to cause volatilization and pyrolysis of the organic binder. Slump and other distortion is avoided by careful selection and control of the rheology, inorganic volume loading, and binder pyrolytic/volatilization characteristics. After binder removal, the preform of packed particulates is then sintered to meld the powder particles, while keeping the shape. In order to control wall sagging, sintering conditions must be closely monitored. The preform is preferably sintered vertically in order to avoid distortion. Sintering condition for PYREX 7761 is approximately 675° C. for 1 hour. At this temperature, glass particle binding occurs and 10–15% shrinkage uniformly occurs throughout the structure. What remains is a glass, glass ceramic, or ceramic depending on the sintering schedule and the composition of the original powder material. For use with this invention, preferably the firing schedule and powder composition should be modified in such a way as to create substantially identical channel walls of high density and no open porosity. The resulting honeycomb block has a plurality of parallel channels or cells extending therethrough. The block may be any length as determined by the point at which it is cut from the extruder.

EXAMPLE

Extrusion and Sintering

Table 1 shows the composition of PYREX 7761 glass. The inorganic powder is made from PYREX 7761 cullet: crushed, magnetically separated, ball milled (alumina), and ultrasonically screened (−325 mesh).

TABLE 1

| Compound | Weight Percent (%) |
| --- | --- |
| $SiO_2$ | 78.92 |
| $K_2O$ | 2.76 |
| $B_2O_3$ | 18.27 |

Table 2 shows the batch composition of the extrudable mixture.

TABLE 2

| Ingredients | Weight (grams) |
| --- | --- |
| PYREX 7761 powder | 7938 |
| Oleic Acid | 80 |
| Dow F-40M METHOCEL | 558 |
| Water (DI) | 1985 |

The inorganic powder, the METHOCEL, and the Oleic Acid are blended together in a LITTLEFORD mixer, and then mulled together with the water addition in a LANCASTER mixer. The mix is then further mixed by evacuation and spaghetti extrusion (3 times). Finally, the batch is extruded through a die to be formed into a multi-celled preform which is cut from the extrudate, ready for sintering.

Table 3 shows the furnace schedule used to sinter the preforms. The preforms are vertically suspended during sintering to minimize bowing.

TABLE 3

| Furnace Schedule |
| --- |
| 1) Room Temperature to 300° C. at 50° C./hr. |
| 2) 300° C. to 550° C. at 20°/hr. |
| 3) 550° C. to 700° C. at 50° C./hr. |
| 4) Hold at 700° C. for 2 hours. |
| 5) 700° C. to Room Temperature (power off). |

Once the preform is sintered, the resulting structure is heated and 15 undergoes a redraw reduction. Redraw takes place approximately at approximately 20° C. to 100° C. above the glass transformation temperature. For PYREX 7761, the sintered block is reheated to 870° C. over approximately 1.5 hours, in order to reach a +/−20° C. temperature uniformity within the section of the block to be stretched. The redraw process occurs in two steps; first, the block is arranged such that the channels are aligned vertically; and, a portion of the extruded block is restrained, while the weight of the structure is allowed to pull the unrestrained portion downward. Second, a constant force is applied to the unrestrained portion to further facilitate the draw. Once the extruded block is stretched to a predetermined diameter, depending on the cross sectional size requirement for the output end of the device, the process is stopped by temperature reduction. This annealing step preferably occurs over one hour in which the temperature is dropped to 20° C. As an example, for a 180 mm long cylindrical block having a 22 mm cross sectional diameter to be drawn to a cross sectional diameter of 4.2 mm, the block must be drawn approximately 920 mm in length. It is preferred that, after redrawing, the length of the capillary reservoir device be between 2 and 3 times the diameter of the block prior to redraw, in order to optimize the liquid retaining capillary characteristics of the individual channels.

In producing a bent reservoir device, as required in some embodiments, the drawn piece is maintained at a temperature of approximately 850° C. in the portion to be bent. The piece is removed from the oven and bent at the appropriate angle, 180° for example. After bending, the piece is placed in an annealing oven in order to cool to room temperature without thermal stress.

After annealing to approximately 20° C. over the course of approximately 1 hour, the piece whether bent or not, is cut on the reduced section of the block, which becomes the output end of the reservoir device, and may also be cut on the loading or input end by a diamond saw for example. The cutting is preferably performed under internal water flux in order to prevent any glass chips or fragments from lodging in the channels. The output end of the piece can then be finished by successively polishing with 12 $\mu$m, 3 $\mu$m, 1 $\mu$m, and 0.3 $\mu$m grit polishing paper. If the device is to be used in printing extremely low volume liquid drops, it is important to achieve a flatness of approximately ±2 $\mu$m across the output end of the device. The device may be further finished under fire polish at approximately 450° C. for one hour.

Optionally, when using a binder such as those disclosed in U.S. Pat. No. 5,602,197, the option exists to redraw the preform after extrusion, but prior to binder removal and sintering Redraw in this case is done as it would be for a thermoplastic polymer; in that the preform, or the section of the preform to be redrawn, is reheated to a softened or partially melted state whereupon the preform is redrawn by stretching. An advantage of using this technique is that inorganic particulates can be used that cannot be redrawn in the inorganic state, such as zirconia, alumina, etc.

In an embodiment in which a capillary reservoir device is made from a thermoplastic polymer, the polymer is initially extruded through a twin screw extruder and die operating at the melting temperature of the thermoplastic material, for example, polypropylene is extruded at approximately 180° C. The target cell density and wall thickness is substantially the same as the glass embodiment discussed above. Once the block has been extruded, the polymer redraw is performed as above and may require external heating of the structure, or the section to be redrawn, to 150° C., for example in polypropylene. The redraw may also require internal heating of the polymer structure by means of forced heated air, for example, in order to preclude any internal heating gradient within the structure during redraw. Although the extrusion has been demonstrated with a polyolefin, specifically, polypropylene, it should be understood that any thermoplastic polymer, as recognized by one skilled in the art, may be used for this process.

Although a cylindrical extrusion is easier to perform in both powdered glass and plastic, a square or rectangular extrusion is preferred in order create a tool capable of depositing a rectilinear array.

Both extrusion of the polymer and the powdered glass is ideally performed by a vertical extrusion process. Vertical extrusion helps reduce problems of wall sagging due to gravitational effects. However, a horizontal extrusion process may be preferred in a mass production setting.

Yet another option for drawing down an extruded cellular body is to fill in the open cells of an extruded preform with a molten wax that exhibits similar plastic properties to the wet batch when solidified. The cooled body, consisting of the wet extruded cellular preform and the solidified plastic wax in the cells, is then pushed through a size reducing die at room temperature. By partially pushing the composite body through a die, a body with the desired transition from large to small cells may be obtained. Afterwards, the wax is melted and removed; then the cellular body is dried, fired and finished in the normal manner. A suitable wax for this technique is a microcrystaline hydrocarbon wax with a high needle penetration hardness (15+). This alternative drawdown technique is more fully disclosed in commonly assigned U.S. pat. application Ser. No. 60/068,230, incorporated herein by reference.

FIG. 1 shows a capillary reservoir device 10 that is the subject of the present invention. In a preferred embodiment, the device ideally comprises a matrix of square channels 12, 100 channels along each outer wall 14 of the structure and 10,000 in total. The top of the device is the fluid loading or input end 16 of the device. The exposed face of the input end shall be called the input face. Each side of the input end 16 of the device is approximately 112.5 mm. The surface area of the entire input face, in this embodiment, is approximately 12,656 mm$^2$. The structure has been redrawn such that the length of each side on the output end 18 of the matrix is approximately 22 mm. The exposed face of the output end shall be called the output face. The surface area of the output face is approximately 484 mm$^2$. Each channel 12 within the device 10 is self contained and decreases in cross sectional area in approximate proportion to the decrease in total cross sectional surface area. Thereby, a channel having a width or pitch of 1.125 mm at the top surface, as in FIG. 1, has a width or pitch of approximately 0.22 mm at the bottom surface. The surface area of a cross-section of one individual channel as a proportion of the cross sectional area of a perpendicular plane taken at any point along the height of the vertical standing device is approximately constant. Wall thickness may increase slightly as a proportion of the total cross sectional area as the device is redrawn, but the number of channels is constant as well as the relative position of each channel in the matrix as defined by the on-center channel to channel pitch. Put another way, the device has a plurality of open ended channels extending from an input face lo an output face wherein at least along a predetermined length, each channel decreases equally in diameter, cross sectional area, and wall thickness.

Figure 22:
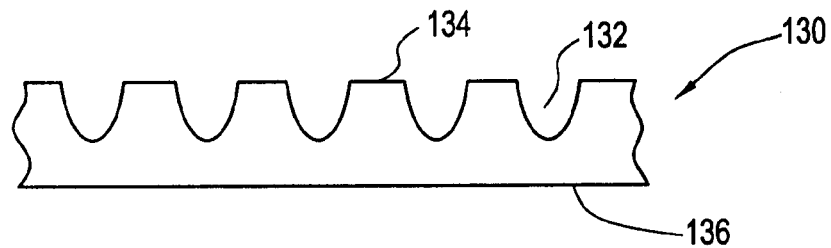
FIG. 22 is a partial cross sectional view of a slab of material which when assembled with other like slabs forms a preform.
Figure 23:
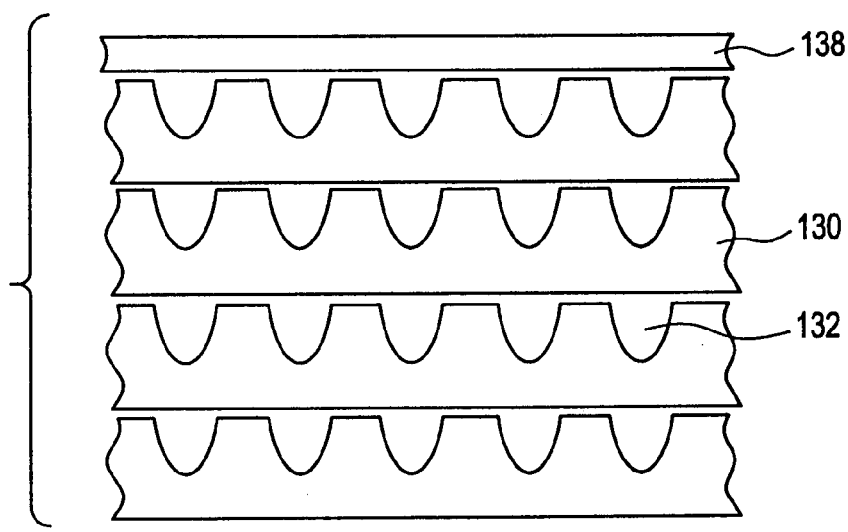
FIG. 23 is a partial cross sectional view of a plurality of slabs piled one upon another and prior to fusion.
Figure 24:
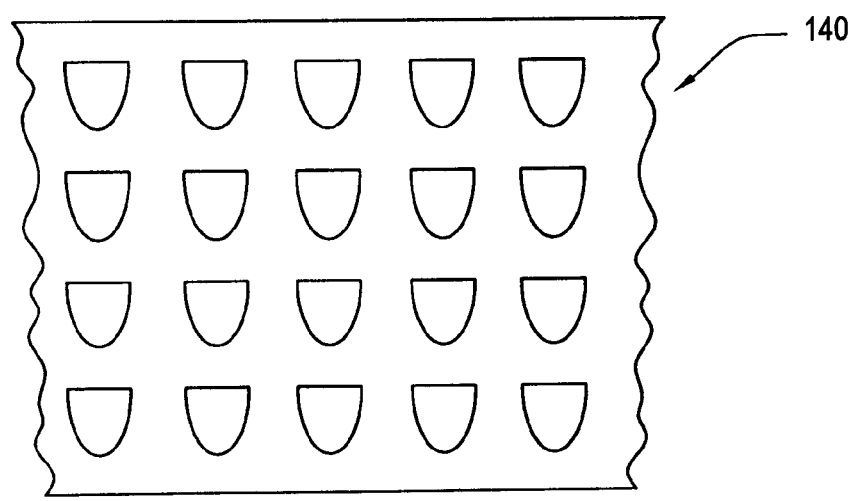
FIG. 24 is a partial cross sectional view of a preform formed by fusing the slabs of FIG. 23.

Another alternative for making a capillary reservoir device is to etch or press channels in a surface of a plurality of slabs, pile the slabs one upon another forming a block having a plurality of channels formed therethrough, fusing the slabs, and redrawing the entire structure. Creating a preform by this method is shown in FIGS. 22 and 23. FIG. 22 shows a cross-sectional view of a portion of a slab 130. The slab 130 has a plurality of evenly spaced parallel channels 132 formed into a top surface 134. The channels can be made by any of a variety of known methods. If the material is glass, the channels may be etched, pressed, or created by precision rolling. If the material is a polymer, the slab may be formed by injection molding techniques, for example. FIG. 23 shows a partial cross sectional view of a plurality of slabs 130 piled one on another. The bottom surface 136 of each slab 130 serves to close the channels 132 of the slab immediately beneath it. A top piece 138 without channels seals the channels of the topmost slab. The entire construct is then heated to a temperature such that the slabs fuse together thereby creating a block 140 capable of being redrawn as shown in FIG. 24. Blocks having any number of channels having any size diameter or shape may be formed using this technique.

Virtually any block made from a thermoplastic material having a plurality of parallel channels formed therethrough may be redrawn in order to form the device of the present invention.

Figure 2:
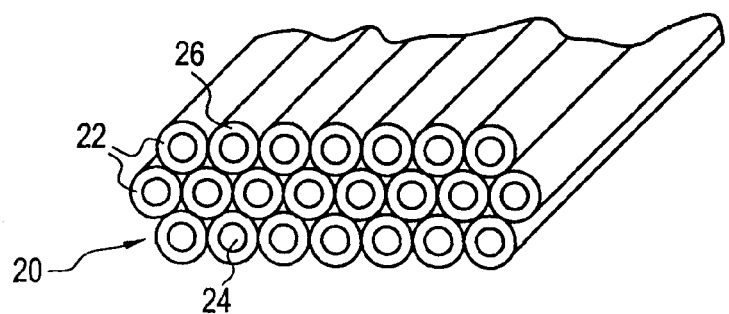
FIG. 2 is a plurality of connected capillary tubes prior to redraw.

It should be noted that an alternative method for making a capillary reservoir device is to bind together a plurality of individual tubes or capillaries. The tubes may be bound together into a bundle having any number of tubes. The bundle is then redrawn and finished in the same fashion as an extruded and redrawn block. FIG. 2 shows the output end 20 of such a bundle of capillary tubes 22 after redraw. The tubes 22 serve the same function as the channels 12 of the device of FIG. 1. But for specific references to figures, the terms channel and tube are analogous hereinafter while describing the device.

As an example to demonstrate feasibility, 22 tubes 22 were bonded together in rows of 7, 8 and 7 tubes. The matrix of 9 mm tubes was then redrawn such that tube to tube center spacing became 350 $\mu$m, and the diameter of the capillary output opening in each tube was 180 $\mu$m.

The planar cut that exposes the output face of the device of either FIG. 1 or FIG. 2, is preferably non-wetting. For example, in FIG. 2, the tube interior 24 preferably has a wetting surface, while the tube ends 26 are preferably non-wetting. Similarly, the interior walls of the channels 12 of the device of FIG. 1 are wetting, while the wall ends are non-wetting. Because of the wetting channel interior and non-wetting end of each channel, droplets of liquid tend to bead on the end of each channel. Further, the non-wetting surface of the entire output plane of the device prevents crosstalk between channels at the output end.

Figure 3:
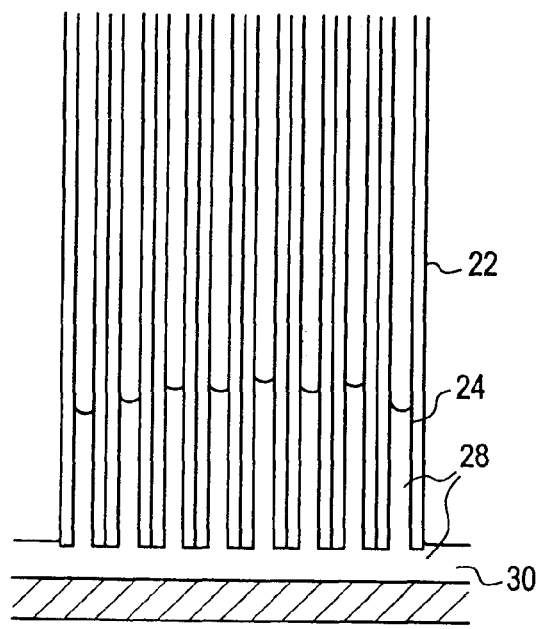
FIG. 3 is an illustration of the output end of the device being dipped into a liquid reservoir in order to impart wettable characteristics to the interior of the channels.
Figure 4:
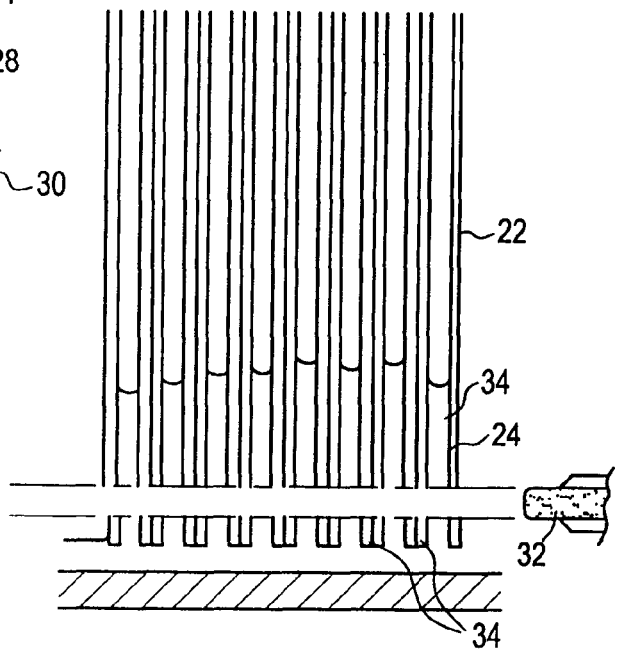
FIG. 4 is an illustration of the output end of the device being trimmed in order to expose a non wetting surface.
Figure 5:
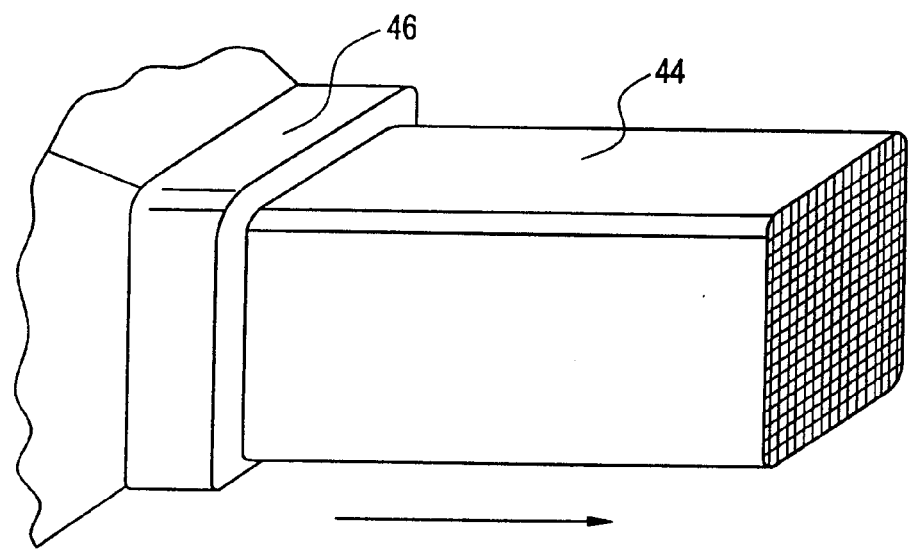
FIG. 5 is a three dimensional view of a preform block of material that is being extruded through a honeycomb die.

Whether the device is made from a redraw of an extruded block or assembled block, or from bonded capillary tubes, the wetting characteristics of the output face may be obtained in the same way. To obtain the wettability characteristics of the output face in a device made of a material that is only moderately wetting, such as polystyrene is to water, or non-wetting such as polyolefins such as polyethylene and polypropylene are to water, wettability can be improved with oxidizing treatments. For example, oxidizing chemical etchants such as sulfuric or chromic acids may be introduced to the channel interiors. One way of subjecting the channel interiors to the oxidizing etchant, or any other liquid that will coat the interior channel walls is illustrated in FIGS. 3–5. FIG. 3 illustrates how liquid 28 from a reservoir 30 coats the interior 24 of the tubes 22 on the output end 20 of the device of FIG. 2. The device is next sliced in a direction perpendicular to the channels' length with a dicing machine as shown in FIG. 4. The dicing exposes the natural non-wetting or less wetting output face of the polymer. FIG. 4 illustrates a planar cut of the output end 20 of the device of FIG. 2 being made with a dicing machine 32. The cut exposes tube ends 26 that are non-wetting, while the tube interior 24 remains wetting due to the coating received from liquid 28 within the reservoir 30. The cut tube fragments 34 are discarded.

With a device made of a naturally wetting material, such as glass is to water, the output portion of the device which has been cut and finished may be pressed against a rubber stamp coated with a non-wetting coating, for example a silane having a $CF_3$ termination, octadecyltriethoxysilane (OTS), or polydimethylsiloxane (PDMS). The silane is transferred to the output face of the device, making the surface non-wetting. The interior of the channels made of class are naturally wetting. Alternatively, the output end may be dipped into a solution that imparts non-wetting characteristics such as fluorodecyltrichlorosilane solution for example, while gas flow is injected into the input end of the capillary array to prevent the solution from entering the channel interiors. This way, output face obtains a non-wetting characteristic, while the channel interiors remain uncoated, and thereby retain their wetting characteristic.

Once formed, the operation of a device whether made of an organic polymer or glass is substantially the same. In operation, fluid is loaded into the input end of the device. The input is compatible with macroscopic fluid loading, and loading may be accomplished through any variety of known means including: pipette, syringe, pumps, multiple pipette or syringe systems, funnels, etc. Preferably, the center spacing between channels at the input end preferably corresponds to the center spacing of a multiwell plate, a 1536 well plate for example. This way, fluids contained individually in each well of a 1536 well plate may be loaded by forcing the fluid through a hole in the bottom of each well in the 1536 well plate into corresponding channels in the capillary reservoir device. Each channel is self contained, so potentially 10,000 different fluids can be loaded into the device. It is important to note that the number of channels is entirely variable and the number 10,000 was chosen simply as an example of a preferred embodiment.

Each channel's volume is determined by its internal dimensions including the height of the device. Ideally, each channel will contain 5 to 500 microliters, but any volume is possible as determined by the variable dimensions: pitch of to channel at top and bottom, and height of the device.

Ideally, the pitch of the channel at the output end is such that liquid will be retained within each channel by capillary force. This way, liquid will remain in each channel until forced out by some external force. One way of forcing liquid through the capillary is though the use of photon pressure to valve the capillaries. In such an embodiment, and as described in French patent appl. No. [r1], an optical pulse is sent through an optical fiber and a microlens through a window in each capillary. The photonic pulse elicits the formation of a droplet from the output end of each capillary that has been designated. Other methods for extracting a droplet from the output end of the capillaries include: external pressure such as a vacuum at the output or a positive pressure at the input end, mechanical pressure, acoustic pressure, magnetic pressure, heating, or any other method that would provide constant displacement among the channels.

In a preferred embodiment, each channel is filled with a different binding entity held within a liquid matrix. "Binding entities" are generally termed as a biological or synthetic molecule having a specific affinity for another molecule, through covalent bonding or non-covalent bonding. Preferably, a specific binding entity contains (either by nature or by modification) a functional chemical group (primary amine, sulfhydryl, aldehyde, etc.), a common sequence (nucleic acids), an epitope (antibodies), a hapten, or a ligand, that allows it to covalently react or non-covalently bond to a common function group on the surface of a substrate. Specific binding entities include, but are not limited to: deoxyribonucleic acids (DNA), ribonucleic acids (RNA), synthetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates and haptens. The term "biomolecule" and "binding entity" are interchangeable for purposes of this disclosure.

It should be noted that application for this device are not limited to biological materials, but may extend to any chemistry capable of being in liquid form or in a suspension including but not limited to emulsions, particle suspensions, and coacervates. In fact, a reservoir device made from PYREX is capable of printing an array of a liquid that has been heated up to 500° C. This has potential implications in chemical applications such as printing room temperature semiconductors, dispensing hot pigments or hot waxes, and other nanoengineered microcomponents.

The liquid that contains the binding entity is preferably an acrylamide monomer, but may be any biocompatible polymerizable material. The acrylamide provides the necessary cross-linking required for DNA or other biomolecule immobilization. In a preferred embodiment, 10,000 different a; ylarnide solutions, each containing an oligimer of slightly different nucleotide sequence are loaded into each channel through means of a multiwell plate as previously described, by multiwell pipette, syringe, etc. Droplets will be elicited from each channel simultaneously by means of photon pressure, external pressure, etc. The drops are contacted against the substrate and thereby deposited. Next, the acrylamide is preferably polymerized by ultra-violet radiation immediately after deposition onto the substrate. The resultant array of polymerized drops is characterized in that the pitch between drops on the substrate is substantially identical to the pitch between channels on the output face of the device. Each droplet occupies an identifiable position in the overall array, and the biomolecules within each drop are covalently bound to the polymerized acrylamide. The biomolecules, in this embodiment-oligonucleotides, are covalently bound to the codeposited polymerized acrylamide.

Any conceivable substrate may be employed in this invention. The substrate may be biological, nonbiological, organic, inorganic, or a combination of any of these, existing as particles, strands, precipitates, gels, sheets, tubing, spheres, beads, porous beads, containers, capillaries, pads, slices, films, plates, slides, membranes, etc. The substrate may have any convenient shape, such as a disc, square, rectangle, sphere, etc. The substrate is preferably flat, but may take on a variety of alternative surface configurations. For example, the substrate may contain raised or depressed regions on which liquid is deposited. Further, the substrate may be glass, polymer or membrane into which channels have been etched; or it may contain regions that have been made porous by means of a chemical etchant. The substrate and its surface preferably form a rigid support on which a liquid with the appropriate surface energy and containing a binding entity can be deposited, and which is preferably functionalized with an organosilane such as gamma-aminopropyl triethoxysilane or methacryloxypropyltriethoxysilane, for example.

In a preferred embodiment, the substrate is flat glass, preferably a borosilicate glass having surface relief features of less than 10 nanometers. Although a non-patterned plate is preferred for droplet alignment issues, the surface of the glass substrate may be coated with, a non-wetting agent such as fluorodecyltrichlorosilane or ocyadecyltrichlorosilane, for example. The coating may be selectively removed by using known methods of photoresist or selectively applied using masking techniques. Preferably, an array of position that are uncoated and thereby wetting is presented. The spacing in the wetting/non-wetting positional array preferably corresponds to the spacing between channels on the output face of the capillary reservoir device. This way, drops need only contact the exposed wetting positions on the substrate for drop transfer. The drops are drawn into the center of the wetting position by physical and chemical means. Crosstalk is eliminated by the wetting characteristics of the substrate. Alternatively, a patterned etching process may create positions within the substrate and below the substrate surface that form a matrix of porous glass regions which may also serve to eliminate the potential for crosstalk. Drops may be deposited within the porous regions which preferably align with the channel spacing on the output face of the capillary reservoir device.

Printing Methods

Printing a matrix of droplets of acrylamide containing oligonucleotides directly from the capillary reservoir device, and with a spacing of less than 200 µm apart, may require a specific process in order to reduce the potential of neighboring droplets from spreading and combining, i.e. crosstalk. The printing process comprises the steps of providing a capillary reservoir device having a non-wetting fluorinated treatment on the output plane and the sidewalls; filling at least one channel of the capillary reservoir device with an acrylamide/biomolecule mixed solution; providing a functionalized glass substrate, for example a substrate coated with an organosilane such as methacryloxypropyltriethoxysilane; and, transferring a droplet from the output of each channel in the device by contact with the substrate in an environment of zero or negative capillary pressure.

An acrylamide/oligonucleotide solution has a medium range surface tension of approximately 52 mN.m$^{-1}$ and a relatively low contact angle on glass substrates functionalized with methacryloxypropyltriethoxysilane, for example, of approximately 50 degrees. Contact angle is a direct measure of surface energy. With a contact angle of 50 degrees, it is not possible to avoid droplet mixing between individual droplets spaced 100 µm or less apart on the substrate prior to curing. Furthermore, contact angles below 90 degrees create, upon transfer, a positive capillary pressure between the capillary reservoir device and the glass substrate which causes the oligonucleotides in the liquid droplets to spread into the gap separating the output end of the capillary reservoir device and the substrate. Therefore, a negative or zero capillary pressure environment is preferred in order to limit crosstalk during drop transfer. In order to achieve a negative or zero capillary pressure environment between the device and the substrate, contact angles equal to or higher than 90 degrees are required on both the output face of the reservoir device and the substrate surface. For the capillary reservoir device, the fluorination treatment previously described satisfies this condition.

For the substrate, the proper contact angle may be achieved by accomplishing the drop transfer from the capillary device to the functionalized substrate in an environmental immiscible liquid medium other than air. Because the oligonucleotides are based in an aqueous solution, alkanes or hydrocarbons satisfy the condition of immiscibility. As an example, the contact angle of the amine functionalized substrate with respect to the oligonucleotide/acrylamide solution is increased from 50 degrees in air to 100 degrees in do lecane. Under these conditions, the spreading of the oligonucleotide/acrylamide droplets is limited and the capillary pressure is negative. By immersing the substrate in the hydrocarbonated liquid, the surface tension of the substrate is substantially reduced compared to air. The contact angle of the oligonucleotide/acrylamide solution to the channels of the reservoir device is also increased, thereby creating favorable conditions for the droplet transfer.

After transfer, the immiscible liquid environment further provides an oxygen free environment for the oligonucleotide/acrylamide droplets to be cured to the substrate. This is an important advantage over open air transfers because the acrylamide polymerization is very sensitive to oxygen inhibition.

In order to increase the contact angle of the functionalized substrate with respect to the oligonucleotide/acrylamide solution to 90 degrees or more, droplet transfer in an immiscible liquid medium having a surface tension of about 35 mN. m$^{-1}$ at 20° C. is preferred.

It has been observed that it may be advantageous to store the functionalized substrate for one hour in the hydrocarbon environment before initiating droplet transfer from the capillary reservoir device. This step allows for the use of hydrocarbonated liquids having a surface tension, γ, of 25 mN. m$^{-1}$ or greater at 20° C. Table 4 is a non-exclusive listing of hydrocarbons that may be used to provide the proper environment for the oligonucleotide/acrylamide droplet deposition onto a substrate.

TABLE 4

| Hydrocarbon | Surface Tension γ at 20° C. (mN.m$^{-1}$) |
| --- | --- |
| Dodecane | 25.4 |
| Tridecane | 26.0 |
| Tetradecane | 26.6 |
| Pentadecane | 27.1 |
| Hexadecane | 27.5 |
| Cyclohexane | 25.2 |
| Decahyronaphthalene | 31.1 |
| Bromonaphthalene | 44.4 |

It should be noted that the process of drop transfer from one medium to another in an environmental immiscible liquid may be performed for any number of differing droplet chemistries and substrates, and may vary according to the chemistry of the droplet as well as the chemistry of the substrate. It may be used wherever low surface tension liquids are being transferred in order to prevent the droplet spreading on the substrate. After the drop is cured, the plate can be warmed up to approximately 60–65° C. In order to evaporate the solvent and/or the environmental hydrocarbon.

Figure 14:
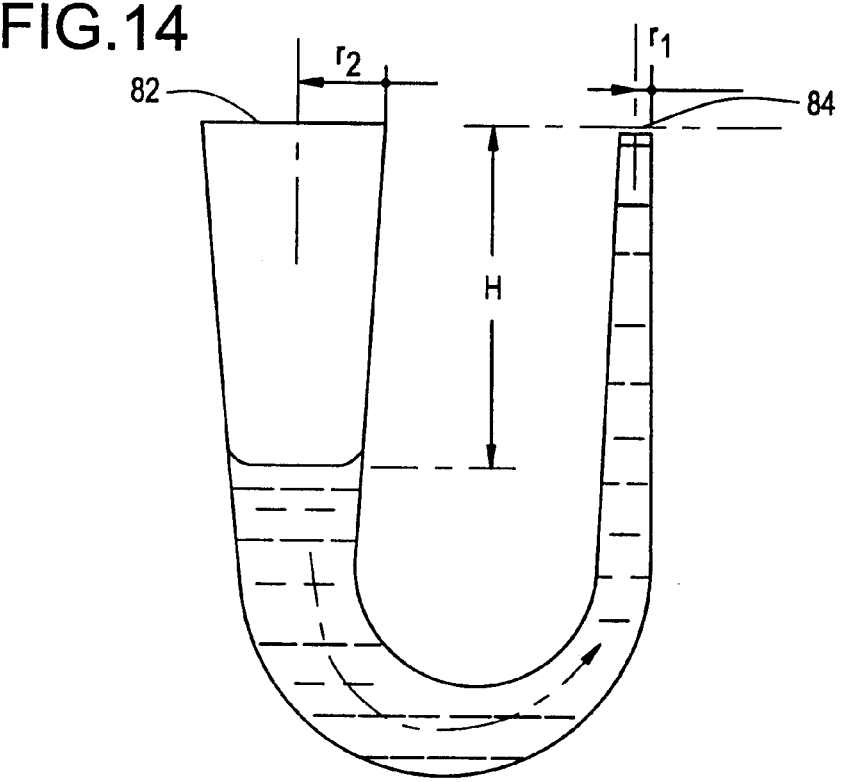
FIG. 14 is a cross sectional view of one channel of an embodiment of the capillary reservoir device of the present invention.

One way of avoiding the need for a negative capillary pressure environment is to create a reservoir device that is designed in such a way as to maintain a constant fluid level at the output end. In explaining the basic concept of how this may be accomplished, the focus will be upon a single channel in the device. In this embodiment, the reservoir is bent after redraw such that the output face and input face are in the same horizontal plane and the entire device is U-shaped. Further, each individual channel is U-shaped, as shown in FIG. 14 which is a cross sectional view of one channel from the device, and has a predetermined radius ($r_2$) at the input end 82 and a predetermined radius ($r_1$) at the output end 84. The liquid may either bead on the output of the channel or form a meniscus within the channel depending on the capillary pressure, density of the liquid and head height as determined by the contact angle. For purposes of this disclosure, whether the liquid beads or not is not important, but in the following examples, the liquid forms a meniscus in the channel.

A pin from a typographic pin plate, for example, is inserted into the channel at the output end of the device in order to pick up a liquid droplet, which in turn is contacted to a substrate in creating the array.

As can be observed, $r_2$ is greater than $r_1$. Liquid, such as DNA probe solution to be printed, is loaded into the input end 82 of the channel. A pin having a radius that is slightly smaller than $r_1$ contacts the liquid by entering the output end 84 of the channel. A liquid droplet, of volume v, is elicited from the channel by surface tension on the pin surface and transferred to a substrate. Due to capillary pressure, the level of liquid in the channel does not drop on the output end. The level of liquid on the input end of the device drops by the volume of the drop that has been removed, while the level of the liquid at the output end of the device remains the same. This phenomenon is a result of the capillary pressure between the output end of the channel and the input end. The capillary pressure is equal to $2\gamma(1/r_1-1/r_2)$, where $r_1<r_2$, and where $\gamma$ is the liquid surface tension. The pressure allows the removal of a volume of liquid, v, at the output end of the channel, without affecting the level of the liquid at the output end. Liquid will be reduced on the input end of the device, while remaining constant on the output end of the device, until the difference in height between the two ends of the capillary, H, reaches the capillary height defined by: $2\gamma/pg$ $(1/r_1-1/r_2)$, where p is the liquid density and g represents gravity (9.81 m.s$^{-2}$). The total volume, V, that may be extracted from the channel before the liquid level on the output end begins to drop is given by the equation: $V=2\pi r_2^2 \gamma (1/r_1-1/r_2)/pg$. The number of possible transfers to a typographic pin from this channel is equal to V/v.

It should be noted that it is not necessary that the input and and output end be in the same horizontal plane. The output end can be lower than the input end, but the distance between the two ends, h, must be less than the capillary height, H. When the output and input ends are in the same plane (h=0), V is at a maximum.

As an example, assuming the input end and the output end are in the same plane (h=0), $r_1=50$ $\mu$m, $r_2=300$ $\mu$m, $\gamma=50\times 10^{-3}$N.m$^{-1}$, and $\rho=10^3$ kg/m$^3$; then the volume of DNA probe solution available, V, while retaining a constant level in the output end of the channel, is equal to 48 $\mu$l. If the typographic plate used to transfer liquid from the output end of the device to a substrate plate has pins having a radius in the order of 40 $\mu$m, the volume of individual droplets will be 80 pl. Therefore, the channel will allow for 600,000 pin transfers of liquid while the liquid level on the output end of the channel remains constant.

Figure 15:
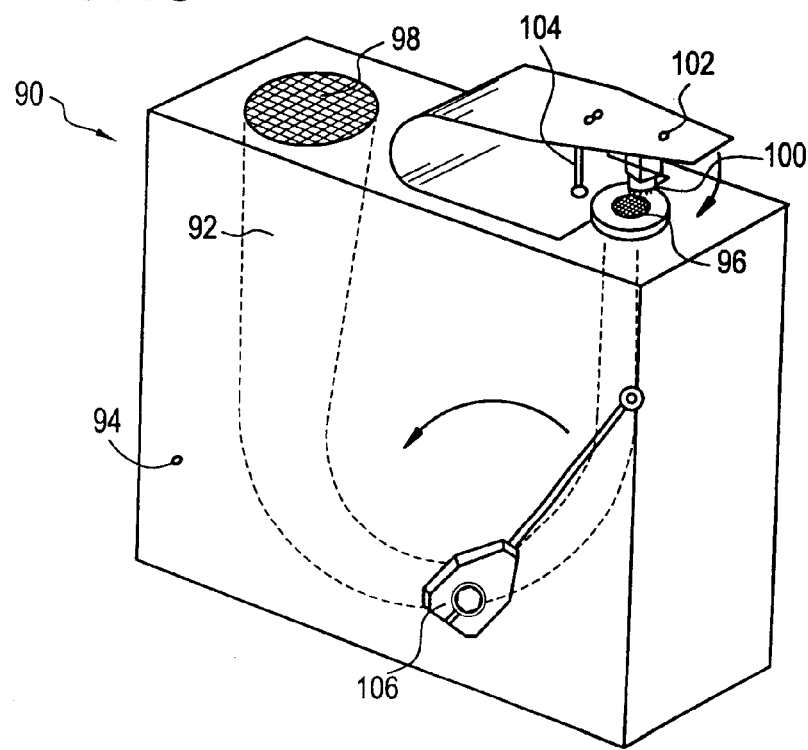
FIG. 15 is a three dimensional view of a printing machine employing the capillary reservoir device of the present invention.
Figure 16:
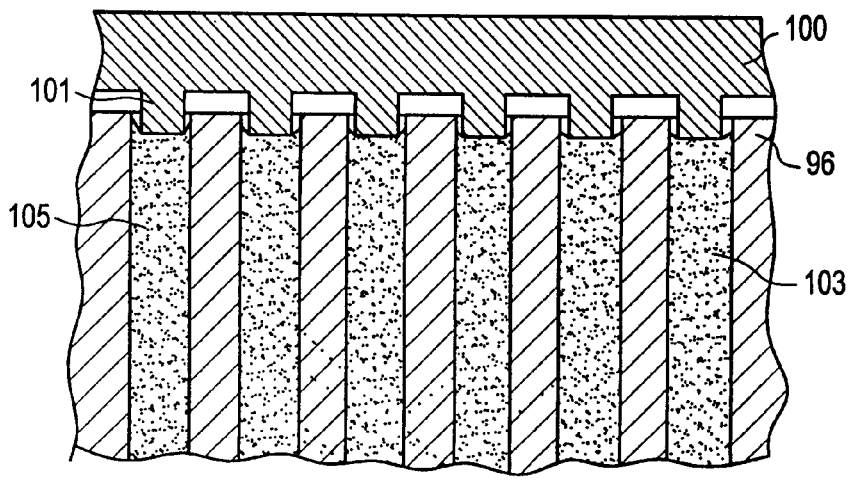
FIG. 16 is a partial cross sectional view of the pin plate of FIG. 15 contacting the output end of the capillary reservoir device.
Figure 17:
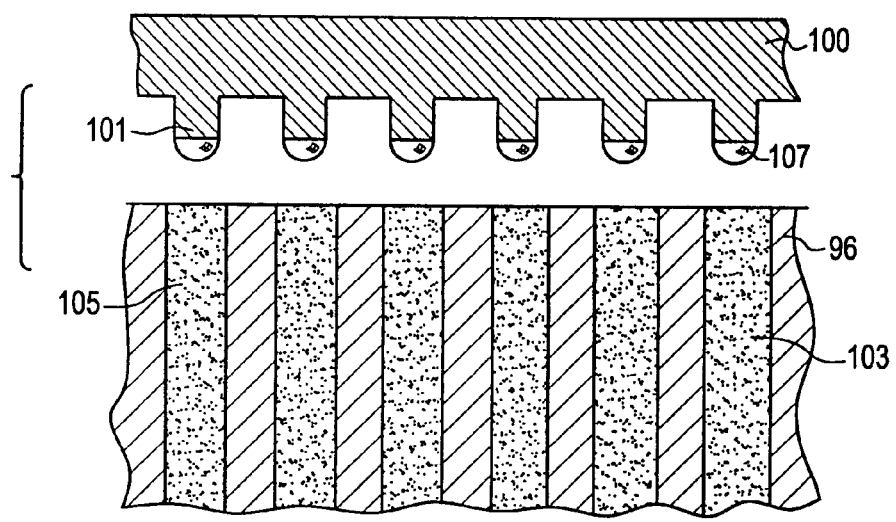
FIG. 17 is a partial cross sectional view of the pin plate of FIG. 16 after removal from the output end of the capillary reservoir device.
Figure 18:
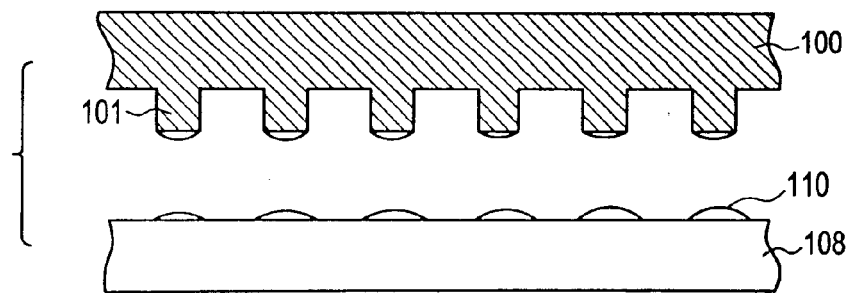
FIG. 18 is a partial cross sectional view of the pin plate of FIGS. 15–17 after deposition of liquid material onto a substrate.

Obviously, the complete reservoir device would be comprised of a plurality of channels having the described U shape. The number of capillaries will correspond to the number of sites in the desired array. An example of a printing tool 90 that employs the bent device is shown in FIG. 15. The bent reservoir device 92 is housed in a boxed unit 94 such that the output face 96 and input face 98 of the device are in approximately the same plane. A typographic pin array 100 having a matrix of pins aligned such that each pin from the matrix fits into a corresponding channel from the output face 96 of the reservoir device 92 is mounted on a flexible stainless steel flextem 102. A string 104 attaches a lever 106 with the top surface of the flextem 102 such that when the lever is actuated, the pin plate 100 contacts the output face 96 of the device such that each pin enters each channel, contacts the liquid therein and is thereafter removed. FIG. 16 shows a cross sectional portion of the pin plate 100 of FIG. 15 as it interacts with the output face 96 of the device. Individual pins 101 contact liquid 103 from a plurality of channels 105. The pin plate 100 is removed from the channels 105 pulling a drop 107 of liquid from each of the channels; the drops are affixed to the ends of the pins 101, as shown in FIG. 17. After the drop 107 is removed, the liquid level remains at the top of each channel 105. A properly prepared substrate is then placed under the pin plate 100; after which, the pin plate is contacted to the substrate surface thereby depositing an array of drops. FIG. 18 shows a partial cross sectional view of a substrate 108 having a plurality of drops 110 that have been deposited thereon by the pin plate 100.

Figure 19:
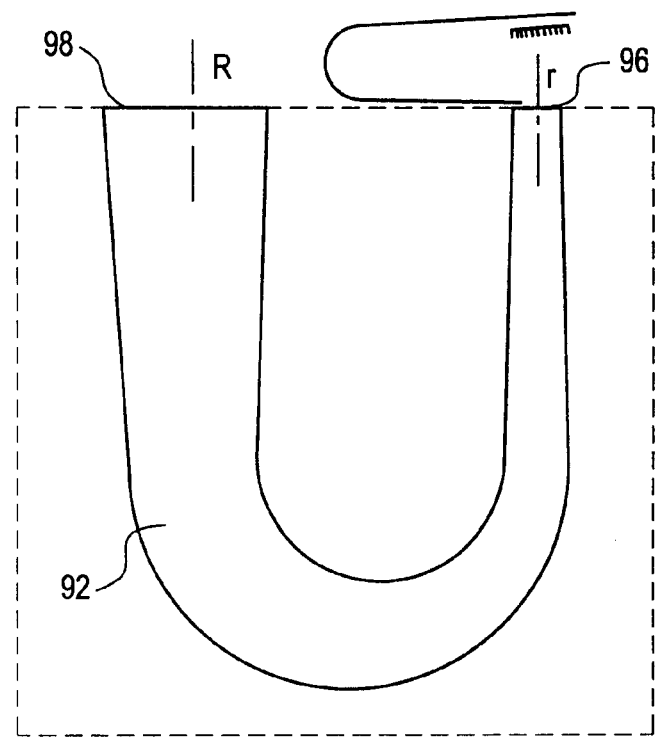
FIG. 19 is a cross sectional view of a printing tool of the present invention.
Figure 20:
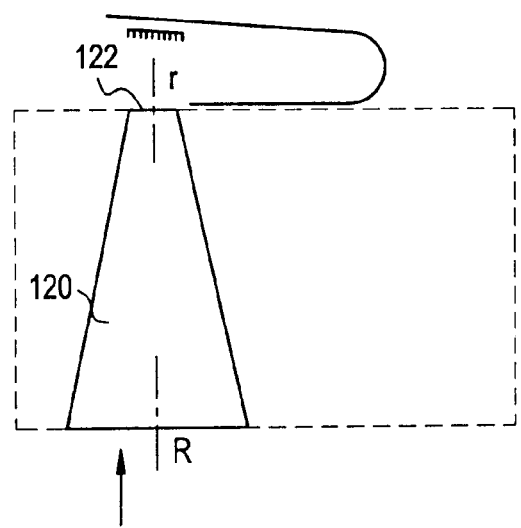
FIG. 20 is a cross sectional view of another embodiment of a printing tool of the present invention.
Figure 21:
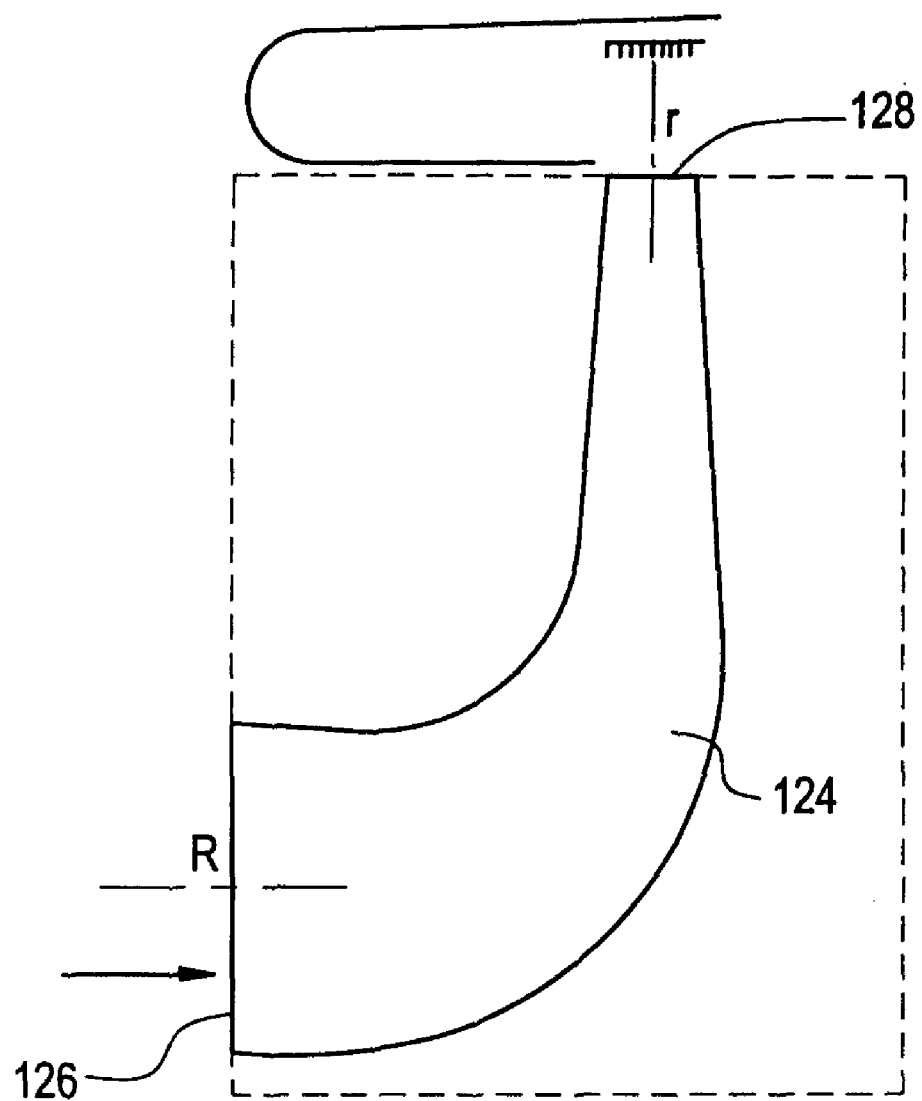
FIG. 21 is a cross sectional view of another embodiment of a printing tool of the present invention.

It is not necessary to employ a U-shaped structure in order to obtain a constant level on output end of the reservoir. A cross section of the printing tool of FIG. 15 containing the U-shaped reservoir device is shown in FIG. 19. Two alternative capillary reservoir designs are shown in FIGS. 20–21. The U-shaped reservoir 92 of FIG. 19 having an input face 98 radius of 300 $\mu$m, an output face 96 radius of 50 $\mu$m, and a length of 200–400 mm, is ideal for containing 50–100$\mu$l of liquid and printing, approximately 500,000–1,000,000 drops of approximately 80 pl/drop. FIG. 20 is an example of a reservoir device having a conical design whereby the input ends of the channels making up the device are filled with the chosen liquid mixture. The device is then flipped over so that the output end of the device faces upward. The liquid will be retained within the channels due to capillary pressure, and the liquid level will remain constant at the output end of the device even after droplets have been drawn from the channel. In this design, assuming the same output and input face radius as above, but having a channel length of 20–50 mm, each capillary reservoir (channel) contains 2–10 $\mu$l of printable liquid, which translates into approximately between 20,000–100,000 drops of 80 pl/drop.

FIG. 21 shows another alternative design of the device. This design allows for greater volume storage than the channel design of FIG. 19, but less than is allowed in the U-shaped design. This L-shaped device 124 works substantially in the same way in that each reservoir is filled through the input face 126 of the device and droplets are drawn from the output end 128 of the device, by pin plate for example. As in the examples above, the liquid level at the output end remains constant. In this design, assuming the same output and input face radius as above, but having a channel length of 50–200 mm each capillary reservoir (channel) contains 10–50 $\mu$l of printable liquid, which translates into approximately between 100,000–500,000 drops of 80 pl/drop.

It should be noted however, that smaller volumes of liquid may be loaded into these devices; the liquid will be driven by capillary forces to the output end of the device. The stated ranges are only suggested volumes and are not intended to be limiting to each embodiment.

Printing Beads

Often, biomolecules such as oligonucleotides or peptides are synthesized on low cross-linked polystyrene beads or other polymeric supports by methods described and referenced by S. R. Wilson and A. W. Czarnik in *Combinatorial Chemistry, Synthesis and Application* (1997). This type of synthesis is called solid phase synthesis and it is by this means that extremely large libraries of biomolucules or other sequentially or combinatorially produced molecules can be synthesized and identified. The synthesized biomolecules are routinely cleaved from the bead at the completion of the synthesis process.

In this embodiment, molecules that have been synthesized by solid phase synthesis are not cleaved from the support beads. Instead, they are incorporated, in suspension, along with an appropriate solvent in order to create a printable liquid. In order to retain the ability to remain in suspension while still minimizing any potential steric interaction problems, the biomolecules are preferably synthesized on beads that are between 0.3 and 0.6 $\mu$m in diameter.

The suspension is printed onto a substrate by the method disclosed above. Preferably and by means of an example, the substrate is glass with a vinyl silane coating and the beads are vinyl benzene cross-linked in divinyl benzene. Each channel of the capillary reservoir device is filled with a different known biomolecule covalently attached to a plurality of beads such that, within any one channel, there are a plurality of identical biomolecules attached to a plurality of beads. The suspensions containing the beads are printed into an array at predetermined attachment positions either on the substrate surface, or within microwells or channels within the substrate. Once printed, the vinyl group from the vinyl silane covalently reacts with the styrene (vinyl benzene) in the bead thereby immobilizing the bead to the substrate surface. The molecules themselves remain immobilized on the bead. It is contemplated that other materials may be used for the beads and for the substrate in order to take advantage of such a covalent bead-substrate immobilization interaction.

In an alternative embodiment, molecules are synthesized on beads that are sized such that only one bead at a time will fit through the output of any individual channel of the device. This way, a single bead may be printed at each position on the array. Each individual bead contains at least one molecule attached thereto, while the bead itself attaches to the substrate. In this embodiment, the sizing of the bead is dependent on the diameter of the channels at the output end of the capillary reservoir device that is employed in the printing.

In yet another embodiment, non-reacted beads are deposited on a substrate in an array. Combinatorial or sequential synthesis can then be performed on the immobilized beads.

Slice Array

Figure 6:
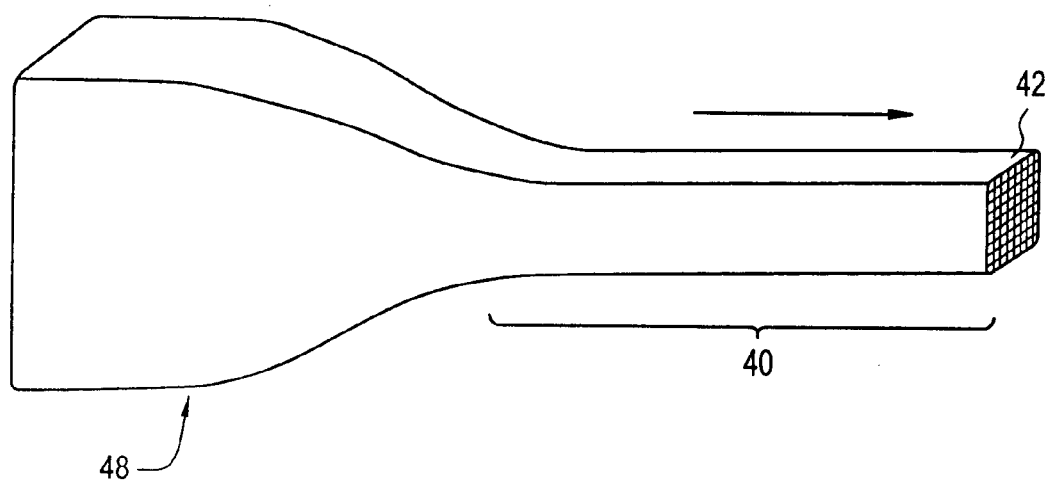
FIG. 6 is a three dimensional view of an extruded block that has been subsequently redrawn.
Figure 7:
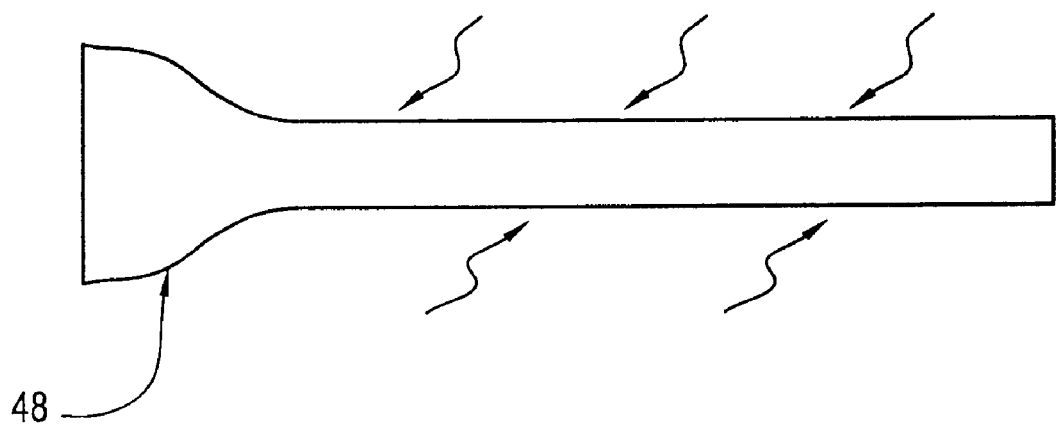
FIG. 7 is a side view of an extruded block that has been subsequently redrawn and is being subjected to a curing process.

Another embodiment of the present invention involves a technique that eliminates the need for liquid handling as between the capillary reservoir device and a substrate. In this embodiment, a capillary reservoir device that preferably has 1,000 or more channels and is preferably comprised of an organic polymer such as polystyrene, is redrawn down (as shown in FIG. 6) to a predetermined size and elongated such that a reduced linear portion 40 of substantially uniform cross sectional size is created at the outlet end 42. FIG. 5 shows the initial extrusion of a preform block 44, through a die 40, and prior to redraw. Each channel of the resultant redrawn device 48 is then filled with a liquid. Each liquid is a different mixture of a particular binding entity and a thermally activated curing polymer such as an epoxy resin (EPON). As an example, each channel may contain a different aminated oligonucleotide or cDNA which is combined with the epoxy resin. An epoxide group from the epoxy resin will covalently react with the amine creating a crosslinked polymer network. A different known oligonucleotide or cDNA fragment is selected for each individual channel and combined with the epoxy. The various mixtures are entered into the many channels, the entire device is cured, for example in a 6 hour cycle at 40° C., or more preferably 2 days at room temperature in order to limit gas production caused by the polymerization reaction. FIG. 7 shows the device of FIG. 6 undergoing a curing step. The curing may be performed by gamma radiation, blue light, temperature activation, or room temperature curing, for example.

After curing, the reduced sized portion 40 is cut from the rest of the device and preferably frozen down to −40° C., below the polymer glass transition temperature. The freezing step makes the epoxy matrix and polymer brittle thereby facilitating a clear cut by fracturing. Cutting by fracturing reduces the chance of crosstalk contamination as between neighboring channels as the blade passes through. Further, deformation or distortion of the array is prevented with this type of cutting technique.

Figure 8:
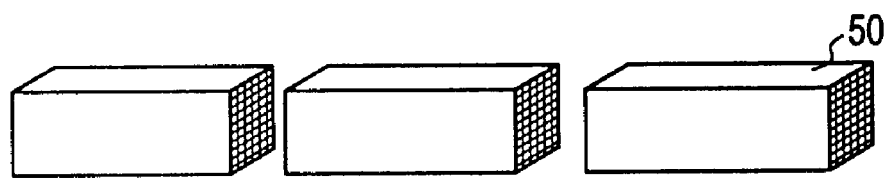
FIG. 8 is a three dimensional view of a series of blocks that have been cut from the redrawn portion of the device of FIG. 7.
Figure 9:
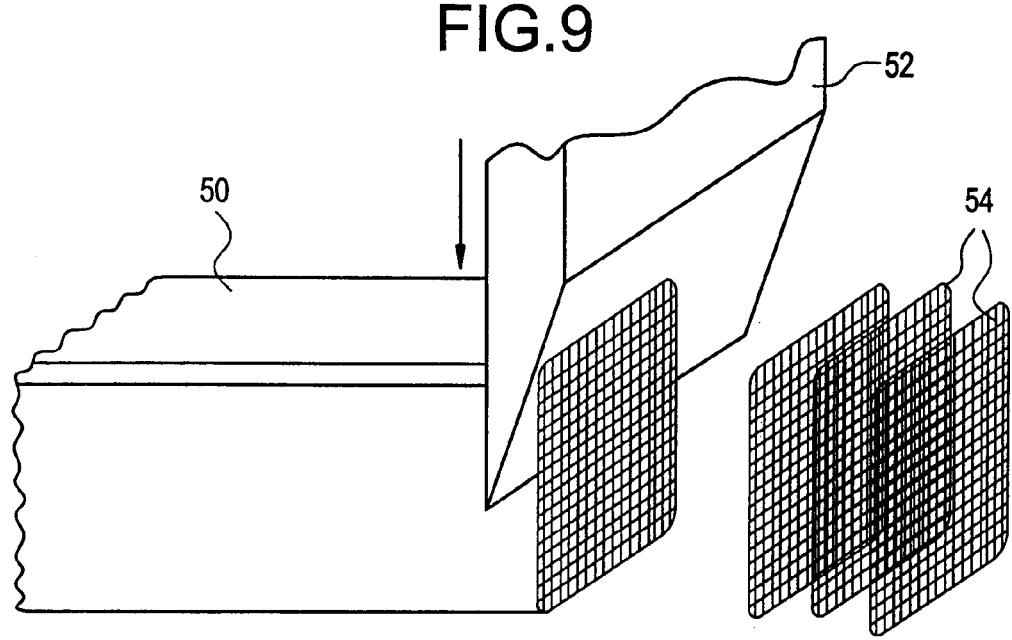
FIG. 9 is a three dimensional view of a block of FIG. 8 being sliced by a blade.

The reduced size portion 40 may then be chopped into blocks 50 as shown in FIG. 8. FIG. 9 shows very fine slices 54 being cut from a frozen block 50 with a tomography cutting tool 52, such as a diamond blade or glass blade, for example. Each slice 54 is preferably approximately between 4 and 10 $\mu$m in thickness, although any slice thickness may be possible. Each slice also contains 10,000 different binding entities suspended in the cured epoxy resin matrix as a result of the channel filling. The slice takes the form of a sheet comprising a lattice network formed by the channel walls and defining a plurality of containment spaces each having sidewalls and an open top and bottom, and a different known binding entity occupying each containment space.

Figure 10:
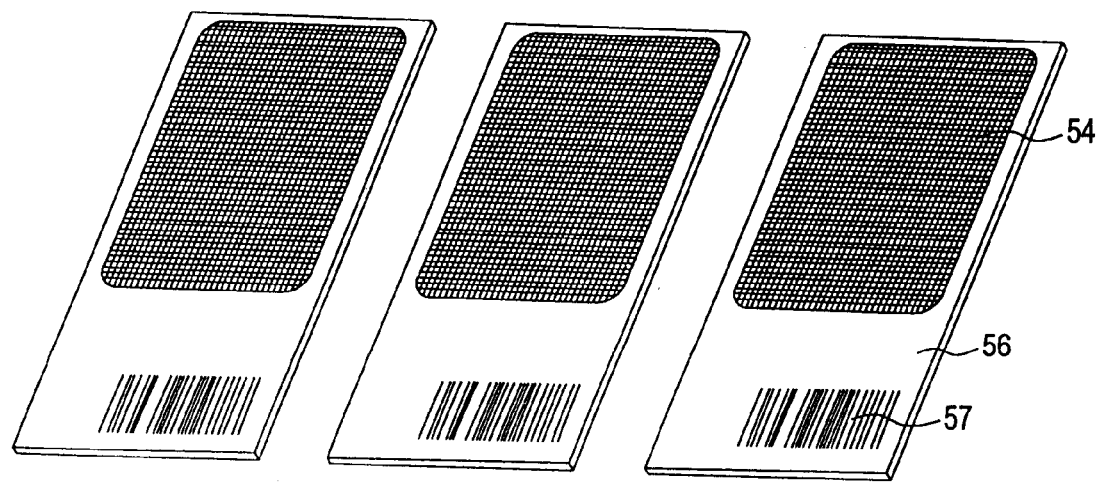
FIG. 10 is a three dimensional view of three high density array plates of the present invention.

After the slicing, the slice 54 is bonded to a preferably flat substrate slide 56, as shown in FIG. 10, preferably made of either glass or an organic polymer, by means of ultrasonic welding or gluing, for example. The walls of the channels serve as boundaries for elimination of crosstalk between samples. Further, the material of the capillary reservoir device is preferably opaque, and more preferably black. This way, optical crosstalk that often results as a consequence of fluorometric, chemiluminescent or colorimetric assays may be reduced as between different samples. Bar coding 57 may be employed as a means of recording the contents of each well or position on the array. Proper alignment of the slice on the substrate can be assured by a feature such as a beveled edge (not shown).

Once bound to the substrate, the slide may be packaged for transport and subsequent use in any variety of research or diagnostic procedures.

It should be noted that as in the method described above, the liquid suspension including synthesized biomolecules covalently attached to beads may be used along with the resin to fill the channels and become part of the polymer network upon curing.

Assay Plate Reformatting

Another embodiment of the present invention involves its use in reformatting assay plates. For many years, multi-well laboratory plates have been manufactured in configurations ranging from 1 well to 96 wells. The wells of multi-well plates are typically used as reaction vessels for performing various tests, growing tissue cultures, screening drugs, or performing analytical and diagnostic functions. Industry standard multi-well plates are laid out with 96 wells in an 8×12 matrix (mutually perpendicular 8 and 12 well rows). In addition, the height, length and width of the 96-well plates are standardized. This standardization has resulted in the development of a large array of auxiliary equipment specifically developed for 96-well formats. The equipment includes devices that load and unload precise volumes of liquid in multiples of 8, 12, or 96 wells at a time. Recently, as sample sizes have been reduced to microliter levels and the demand for a greater number of tests per plate has increased, the number of wells on a plate have likewise increased, e.g. from 384 wells to 1536 wells and above. In order to accommodate the existing auxiliary equipment, the standard plate footprint has remained the same, while the well density has increased. The higher density plates predominately have a number of wells that are a multiple of the standard 96. These plates have well spacing that is fractionally based on the center well spacing of a 96 well plate.

Figure 11:
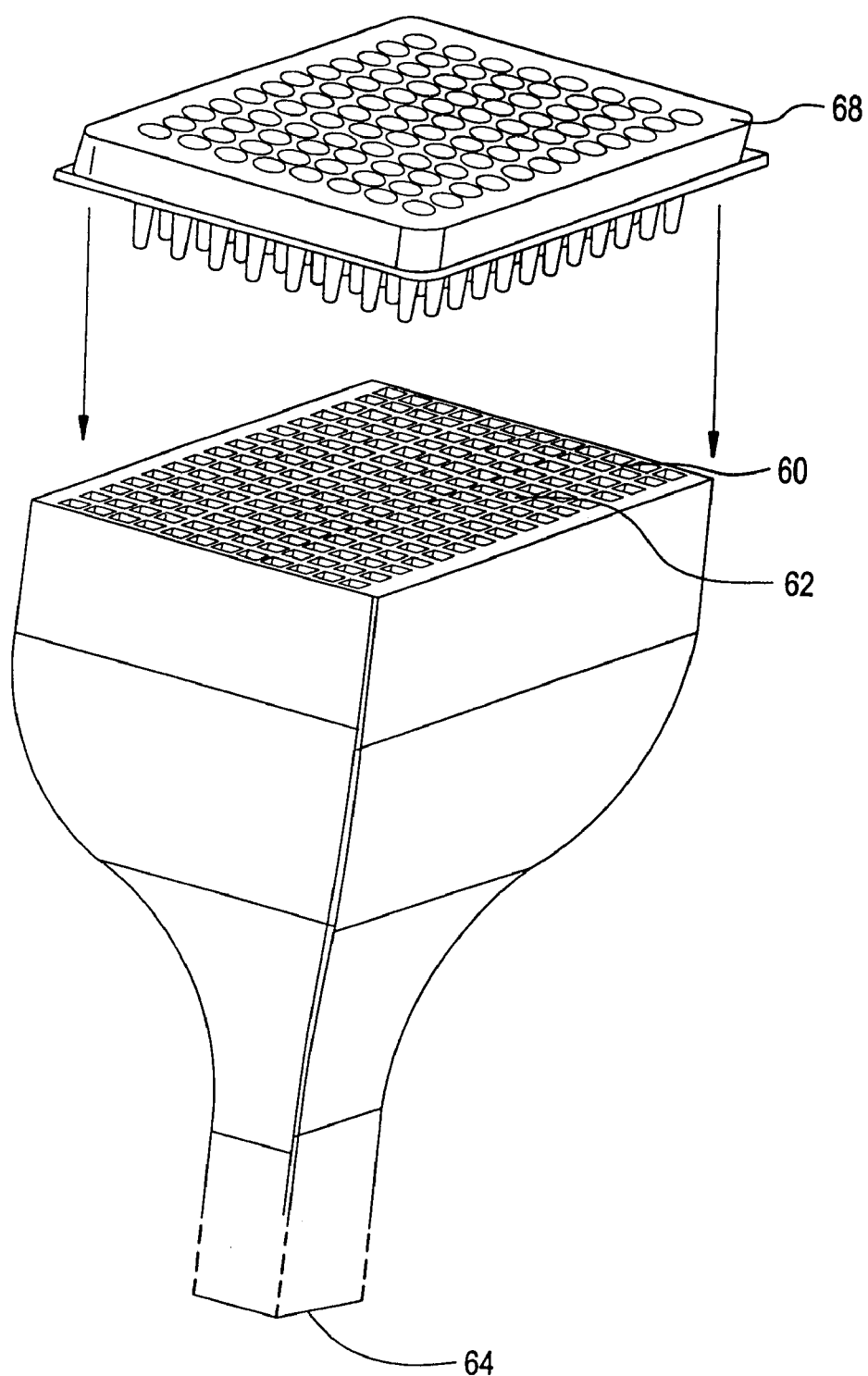
FIG. 11 is an exploded view of a method of transfer of liquid sample from a multiwell plate to the capillary reservoir device of the present invention.

One challenge that has presented scientists is how to efficiently and quickly transfer samples that have been prepared in a comparatively lower density plate, such as a 96 well plate, to a plate of comparatively more wells per same unit area, such as a 1536 well plate, for example. Referring to FIG. 11, a redrawn capillary device can be formed having such dimensions that the transfer form a 96 well plate to a 1536 well plate can occur quickly and easily. The input end 60 of the device is sized approximately to the dimensions of an industry standard 96 well plate (3.370 inches by 5:035 inches). 96 channels 62 are spaced in an 8×12 matrix (mutually perpendicular 8 and 12 channel rows). The channels align with the wells of the 96 well plate which are spaced approximately 0.355 inches on center. The device is redrawn in a 16 to 1 reduction such that the center spacing between channels on the output end 64 approximately equates to the center spacing between wells of a 1536 well plate (0.089 inches). The wells of a 1536 well plate are spaced in a 48×32 matrix (mutually perpendicular 48 and 32 well rows). It would take 16 of the 96 well plates to fill a plate having 1536 wells. The samples that have been transferred will have an ordered orientation. In other words, the 1536 well plate can be divided into a matrix of 4 rows and 4 columns, each location in the matrix containing the samples from a single 96 well plate in their original orientation.

Figure 12:
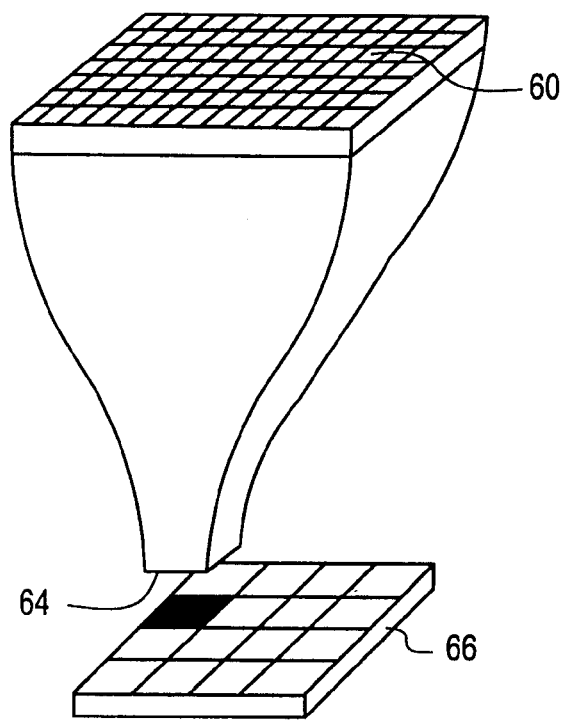
FIG. 12 is a three dimensional view of the device of FIG. 11 as used to deposit liquid sample to a receiving plate.
Figure 13:
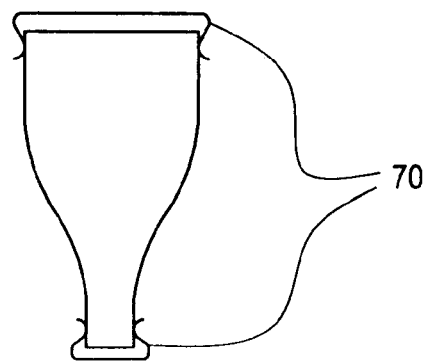
FIG. 13 is a cross sectional view of a capillary reservoir device of the present invention engaged by sealing means on both ends.

In FIG. 11, a 96 well filter plate 68 is aligned over the input end 60 of the device. Each well from the 96 well filter plate 68 aligns with a channel from the device. Samples from the 96 well filter plate are loaded into each channel 62. The output end 64 of the device is then located over a portion of a 1536 well plate 66 as shown in FIG. 12 such that channels on the output end 64 align with wells of the 1536 well plate. Sample is then expelled from each channel into individual wells of the plate 66.

The output end of the device may be fitted with multiple syringe needles or pipette tips to facilitate transfer.

Use of this transfer method is especially beneficial for dispensing large numbers of samples in compiling multiple copies of a compound library, for to example.

The capillary device used as a transfer tool works equally well for transfers between a 96 well plate and a 384 well plate. The reduction during redraw in this case is 4 to 1. The 384 well plate can contain the samples from four 96 well plates in a 2×2 matrix. The capillary device may be employed to deliver samples from a multiwell plate of having any number of wells to a plate having a larger number of well per unit area. The device may even be employed in the reverse, to transfer samples from a 1536 well plate to a 96 well plate, for example.

Further, it can be conceived that sealing means can be provided that can cover both the loading or input end of the device and the output end of the device. Such a seal will prevent evaporation and create favorable storage conditions. Examples of sealing means include snap-on lids, heat sealed wraps, rubber mats, pressure sealing tape, or any other sealing mechanism known in the art.

Further, the reformatting tool can be used as between a 384 well plate and a 1536 well plate; or even from a 1536 to a flat substrate. It is conceived that the reformatting tool can be used as between any two plates of differing well density, so long as the matrix pattern defined by the pitch between wells in the plates is scaled.

It can be further conceived that semi-conductor microfabrication may be accomplished using the redraw and printing technology disclosed herein. Although the invention has been described in detail for the purpose of illustration, it is understood that such detail is solely for that purpose and variations can be made therein by those skilled in the art without departing from the spirit and scope of the invention which is defined by the following claims.

What is claimed is:

1. A method for transferring individual droplets of liquid to a substrate, comprising:

providing a reservoir device having a plurality of individual passages, each passage having an input end and an output end of smaller cross sectional area than the input end;

positioning a transfer device having an array of pins extending therefrom such that the pins face the output ends of the passages;

contacting the pins with liquid from the corresponding passages to transfer droplets of liquid from the corresponding passages to the pins; and moving the pins relative to the substrate to transfer the droplets of liquid onto the substrate.

2. A method for transferring individual droplets of liquid to a substrate, comprising:

providing a reservoir device having a plurality of individual passages, each passage having an output end and decreasing in cross sectional area along at least a portion of the passage in a direction toward the output end;

positioning a transfer device having an array of pins extending therefrom such that the pins face the output ends of the passages;

contacting the pins with liquid from the corresponding passages to transfer droplets of liquid from the corresponding passages to the pins; and moving the pins relative to the substrate to transfer the droplets of liquid onto the substrate.

3. A method for transferring individual droplets of liquid to a substrate, comprising:

providing a rescrvoir device having a plurality of individual passages, each passage having an output end, a density of the passages in the reservoir device increasing along at least a portion thereof in a direction toward the output ends of the passages;

positioning a transfer device having an array of pins extending therefrom such that the pins face the output ends of the passages;

contacting the pins with liquid from the corresponding passages to transfer droplets of liquid from the corresponding passages to the pins; and moving the pins relative to the substrate to transfer the droplets of liquid onto the substrate.

4. The method of any one of claims 1–3, wherein the contacting step includes moving the pins into contact with liquid from the corresponding passages.

5. The method as claimed in any one of claims 1–3, wherein the moving step includes moving the pins a sufficient distance such that the droplets of liquid directly contact the substrate.

6. The method as claimed in any one of claims 1–3, wherein the contacting step includes transferring droplets of liquid from the corresponding passages to tips of the pins.

7. The method as claimed in any one of claims 1–3, wherein the transfer device is a typographic pin plate.

8. The method as claimed in any one of claims 1–3, wherein the providing step includes providing a reservoir device in which a ratio of a cross sectional area of a passage relative to a cross sectional area of the reservoir device is substantially identical at a liquid-input end of the reservoir device and a liquid-output end of the reservoir device.

9. A method for transferring individual droplets of liquid to a substrate, comprising:
  providing a reservoir device having a plurality of individual passages, each passage having an input end and an output end of smaller cross sectional area than the input end;
  positioning a transfer device having an array of pins extending therefrom such that the pins face the output ends of the passages;
  contacting the pins with liquid from the corresponding passages to transfer droplets of liquid from the corresponding passages to the pins; and
  moving the pins relative to the substrate to transfer the droplets of liquid onto the substrate,
  wherein the providing step includes bundling a plurality of capillary tubes, and redrawing the bundled capillary tubes.

10. A method for transferring individual droplets of liquid to a substrate, comprising:
  providing a reservoir device having a plurality of individual passages, each passage having an input end and an output end of smaller cross sectional area than the input end;
  positioning a transfer device having an array of pins extending therefrom such that the pins face the output ends of the passages;
  contacting the pins with liquid from the corresponding passages to transfer droplets of liquid from the corresponding passages to the pins; and
  moving the pins relative to the substrate to transfer the droplets of liquid onto the substrate,
  wherein the providing step includes extruding a material through a multi-cell die to create a multi-celled honeycomb structure, and redrawing at least a portion of the honeycomb structure.

11. The method of claim 10, wherein the providing step further includes cutting the redrawn portion in a direction perpendicular to a longitudinal direction of the passages to expose a face having a cross sectional area less than a cross sectional area of the extruded honeycomb structure.

12. A method for transferring individual droplets of liquid to a substrate, comprising:
  providing a reservoir device having a plurality of individual passages, each passage having an input end and an output end of smaller cross sectional area than the input end;
  positioning a transfer device having an array of pins extending therefrom such that the pins face the output ends of the passages;
  contacting the pins with liquid from the corresponding passages to transfer droplets of liquid from the corresponding passages to the pins; and
  moving the pins relative to the substrate to transfer the droplets of liquid onto the substrate,
  wherein the providing step includes extruding material through a die thereby forming a block having the passages, and redrawing the block such that a circumference of the block is reduced.

13. A method for transferring individual droplets of liquid to a substrate, comprising:
  providing a reservoir device having a plurality of individual passages, each passage having an input end and an output end of smaller cross sectional area than the input end;
  positioning a transfer device having an array of pins extending therefrom such that the pins face the output ends of the passages;
  contacting the pins with liquid from the corresponding passages to transfer droplets of liquid from the corresponding passages to the pins; and
  moving the pins relative to the substrate to transfer the droplets of liquid onto the substrate,
  wherein the positioning step includes positioning the pins opposite the output ends of the passages, and wherein the method further comprises the step of positioning the substrate between the pins and the output ends of the passages prior to moving the pins relative to the substrate.

14. An apparatus for transferring individual droplets of liquid to a substrate, comprising:
  a reservoir device having a plurality of individual passages, each of the passages having an input end and an output end of smaller cross sectional area than the input end; and
  a transfer device having an array of pins extending therefrom, the transfer device positionable such that the pins face the output ends of the passages, the pins being adapted to receive liquid from corresponding passages for transfer of individual droplets of liquid to the substrate.

15. An apparatus for transferring individual droplets of liquid to a substrate, comprising:
  a reservoir device having a plurality of individual passages, each passage being isolated from each other passage, each passage having an output end and decreasing in cross sectional area along at least a portion of the passage in a direction toward the output end; and
  a transfer device having an array of pins extending therefrom, the transfer device positionable such that the pins face the output ends of the passages, the pins being adapted to receive liquid from corresponding passages and to transfer individual droplets of liquid to the substrate.

16. An apparatus for transferring individual droplets of liquid to a substrate, comprising:
  a reservoir device having a plurality of individual passages, each passage having an output end, the density of the passages in the reservoir device increasing along at least a portion thereof in a direction toward the output ends of the passages; and
  a transfer device having an array of pins extending therefrom, the transfer device positionable such that the pins face the output ends of the passages, the pins being adapted to receive liquid from corresponding passages for transfer of individual droplets of liquid to the substrate.

17. The apparatus as claimed in any one of claims 14–16, wherein the reservoir device is a monolithic structure.

18. The apparatus as claimed in anyone of claims 14–16, further comprising a drive member adapted to move the pins relative to the corresponding passages.

19. The apparatus as claimed in any one of claims 14–16, wherein the pins are dimensioned to enter the corresponding passages.

20. The apparatus as claimed in any one of claims 14–16, wherein the passages are configured to prevent fluid communication therebetween.

21. The apparatus as claimed in any one of claims 14–16, wherein a ratio of a cross sectional area of a passage relative to a cross sectional area of the reservoir device is substantially identical at a liquid-inlet end of the reservoir device and at a liquid-output end of the reservoir device.

22. The apparatus as claimed in any one of claim 14–16, wherein the reservoir device has an input and an output in a different plane from the input.

23. The apparatus as claimed in claim 14, wherein the input end of each passage is in a different plane from the output end.

24. The apparatus as claimed in any one of claims 15–16, wherein the passages of the reservoir device have an input end in a different plane from the output end.

25. The apparatus as claimed in any one of claims 14–16, wherein the pins are dimensioned to extend into the output ends of the corresponding passages.

26. The apparatus as claimed in any one of claims 14–16, wherein the passages have interior walls having a wetting surface, and the output ends of the passages have a non-wetting end surface.

27. The apparatus as claimed in any one of claims 14–16, wherein the reservoir device is comprised of an organic polymer.

28. The apparatus as claimed in any one of claims 14–16, wherein the reservoir device is comprised of an inorganic polymer.

29. The apparatus as claimed in claim 28, wherein the inorganic polymer is glass.

30. The apparatus as claimed in any one of claims 14–16, wherein the reservoir device contains approximately 10,000 passages.

31. The apparatus as claimed in any one of claims 14–16, wherein the pins are adapted to receive liquid on tips of the pins.

32. The apparatus as claimed in any one of claims 14–16, wherein the transfer device is a typographic pin plate.

33. An apparatus for transferring individual droplets of liquid to a substrate, comprising;
   a reservoir device having a plurality of individual passages, each of the passages having an input end and an output end of smaller cross sectional area than the input end; and
   a transfer device having an array of pins extending therefrom, the transfer device positionable such that the pins face the output ends of the passages, the pins being adapted to receive liquid from corresponding passages for transfer of individual droplets of liquid to the substrate,
      wherein the reservoir device has an input and an output in the same plane as the input.

34. The apparatus as claimed in claim 33, wherein the reservoir device has a substantially U-shape.

35. An apparatus for transferring individual droplets of liquid to a substrate, comprising:
   a reservoir device having a plurality of individual passages, each of the passages having an input end and an output end of smaller cross sectional area than the input end; and
   a transfer device having an array of pins extending therefrom, the transfer device positionable such that the pins face the output ends of the passages, the pins being adapted to receive liquid from corresponding passages for transfer of individual droplets of liquid to the substrate,
   wherein the reservoir device has an input and an output in a different plane from the input, and
   wherein the reservoir device has a substantially conical shape.

36. An apparatus for transferring individual droplets of liquid to a substrate, comprising:
   a reservoir device having a plurality of individual passages, each of the passages having an input end and an output end of smaller cross sectional area than the input end; and
   a transfer device having an array of pins extending therefrom, the transfer device positionable such that the pins face the output ends of the passages, the pins being adapted to receive liquid from corresponding passages for transfer of individual droplets of liquid to the substrate,
   wherein the reservoir device has an input and an output in a different plane from the input, and
   wherein the reservoir device has a substantially L-shape.

37. The apparatus as claimed in any one of claims 33, 35, and wherein the reservoir device is approximately one inch square at the output ends of the passages.

38. The apparatus as claimed in any one of claims 33, 35, and 36, wherein the pins have a radius less than 50 µm.

39. The apparatus as claimed in any one of claims 33, 35, and 36, wherein the pins have a radius of about 40 µm.

40. The apparatus as claimed in any one of claims 33, 35, and 36, further comprising a boxed unit in which the reservoir device is mounted.

41. The apparatus as claimed in any one of claims 33, 35, and 36, wherein each passage is dimensioned to contain 5 to 500 microliters of liquid.

42. An apparatus for transferring individual droplets of liquid to a substrate, comprising:
   a reservoir device having a plurality of individual passages, each of the passages having an input end and an output end of smaller cross sectional area than the input end; and
   a transfer device having an array of pins extending therefrom, the transfer device positionable such that the pins face the output ends of the passages, the pins being adapted to receive liquid from corresponding passages for transfer of individual droplets of liquid to the substrate,
   wherein the passages are defined by redrawn capillary tubes.

43. An apparatus for transferring individual droplets of liquid to a substrate, comprising:
   a reservoir device having a plurality of individual passages, each of the passages having an input end and an output end of smaller cross sectional area than the input end; and
   a transfer device having an array of pins extending therefrom, the transfer device positionable such that the pins face the output ends of the passages, the pins being adapted to receive liquid from corresponding passages for transfer of individual droplets of liquid to the substrate,
   wherein the input end of each passage is in the same plane as the output end.

44. An apparatus for transferring individual droplets of liquid to a substrate, comprising:
- a reservoir device having a plurality of individual passages, each passage having an output end and decreasing in cross sectional area along at least a portion of the passage in a direction toward the output end; and
- a transfer device having an array of pins extending therefrom, the transfer device positionable such that the pins face the output ends of the passages, the pins being adapted to receive liquid from corresponding passages for transfer of individual droplets of liquid to the substrate,
- wherein the passages of the reservoir device have an input end in the same plane as the output end.

45. An apparatus for transferring individual droplets of liquid to a substrate, comprising:
- a reservoir device having a plurality of individual passages, each of the passages having an input end and an output end of smaller cross sectional area than the input end; and
- a transfer device having an array of pins extending therefrom; the transfer device positionable such that the pins face the output ends of the passages, the pins being adapted to receive liquid from corresponding passages for transfer of individual droplets of liquid to the substrate,
- wherein the passages of the reservoir device form a substantially U-shape.

46. An apparatus for transferring individual droplets of liquid to a substrate, comprising:
- a reservoir device having a plurality of individual passages, each passage having an output end and decreasing in cross sectional area along at least a portion of the passage in a direction toward the output end; and
- a transfer device having an array of pins extending therefrom, the transfer device positionable such that the pins face the output ends of the passages, the pins being adapted to receive liquid from corresponding passages for transfer of individual droplets of liquid to the substrate,
- wherein the passages of the reservoir device have an input end in a different plane from the output end, and
- wherein the reservoir device has a substantially conical shape.

47. An apparatus for transferring individual droplets of liquid to a substrate, comprising:
- a reservoir device having a plurality of individual passages, each passage having an output end and decreasing in cross sectional area along at least a portion of the passage in a direction toward the output end; and
- a transfer device having an array of pins extending therefrom, the transfer device positionable such that the pins face the output ends of the passages, the pins being adapted to receive liquid from corresponding passages for transfer of individual droplets of liquid to the substrate,
- wherein the passages of the reservoir device have an input end in a different plane from, the output end, and
- wherein the reservoir device has a substantially L-shape.

48. An apparatus for transferring individual droplets of liquid to a substrate, comprising:
- a reservoir device having a plurality of individual passages, each of the passages having an input end and an output end of smaller cross sectional area than the input end;
- a transfer device having an array of pins extending therefrom, the transfer device positionable such that the pins face the output ends of the passages, the pins being adapted to receive liquid from corresponding passages for transfer of individual droplets of liquid to the substrate; and
- a drive member adapted to move the pins relative to the corresponding passages,
- wherein the pins are mounted on a flexible mount, and the drive member is coupled to the flexible mount to flex the pins toward the output ends of the corresponding passages.

49. A reservoir device for use in transferring a high density biological or chemical array of individual droplets of liquid to a substrate, comprising:
- a plurality of passages collectively foaming a matrix having a plurality of rows and columns, each of the passages having an input end and an output end, the passages being spaced apart by a center-to-center distance measured from the center of one passage to the center of an adjacent passage, the center-to-center distance between adjacent passages being larger between respective input ends than between respective output ends.

50. The reservoir device as claimed in claim 49, wherein, along at least a portion of the adjacent passages, the center-to-center distance between the adjacent passages decreases uniformly.

51. The reservoir device as claimed in claim 49, wherein the output end of each of the passages has a smaller cross sectional area than the input end.

52. The reservoir device as claimed in claim 49, wherein each of the passages decreases in cross sectional area along at least a portion of the passage in a direction toward the output end.

53. The reservoir device as claimed in claim 49, wherein a density of the passages in the reservoir device increases along at least a portion thereof in a direction toward the output ends of the passages.

54. The reservoir device as claimed in claim 49, wherein a ratio of a cross sectional area of a passage relative to a cross sectional area of the reservoir device is substantially identical at a liquid-input end of the reservoir device and a liquid-output end of the reservoir device.

55. The reservoir device as claimed in claim 49, wherein the passages are configured to prevent fluid communication therebetween.

56. The reservoir device as claimed in claim 54, wherein the reservoir device is approximately one inch square at the liquid-output end.

57. The reservoir device as claimed in claim 49, wherein the passages have interior walls having a wetting surface, and the output ends of the passages have a non-wetting end surface.

58. The reservoir device as claimed in claim 49, wherein the reservoir device is comprised of an organic polymer.

59. The reservoir device as claimed in claim 49, wherein the reservoir device is comprised of an inorganic polymer.

60. The reservoir device as claimed in claim 59, wherein the inorganic polymer is glass.

61. The reservoir device as claimed in claim 49, wherein the reservoir device contains approximately 10,000 passages.

62. The reservoir device as claimed in claim 49, wherein each passage is dimensioned to contain 5 to 500 microliters of liquid.

63. The reservoir device as claimed in claim 49, wherein the center-to-center distance is approximately 220 $\mu$m at the output ends of the passages.

64. The reservoir device as claimed in claim 49, wherein the center-to-center distance is approximately 350 µm at the output ends of the passages.

65. The reservoir device as claimed in claim 49, wherein the output end of each of the passages has a diameter of approximately 180 µm.

66. The reservoir device as claimed in claim 49, wherein the matrix is formed by a redrawn extruded material.

67. The reservoir device as claimed in claim 49, wherein the matrix is formed by bundled, redrawn capillary tubes.

* * * * *